(12) United States Patent
True et al.

(10) Patent No.: US 9,950,158 B2
(45) Date of Patent: Apr. 24, 2018

(54) DIRECTIONAL FEATURES FOR IMPLANTABLE MEDICAL LEADS

(71) Applicants: Kyle True, Coon Rapids, MN (US); Brian Soltis, St. Paul, MN (US)

(72) Inventors: Kyle True, Coon Rapids, MN (US); Brian Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 310 days.

(21) Appl. No.: 13/721,923

(22) Filed: Dec. 20, 2012

(65) Prior Publication Data
US 2013/0166007 A1 Jun. 27, 2013

Related U.S. Application Data

(60) Provisional application No. 61/578,628, filed on Dec. 21, 2011, provisional application No. 61/599,060, filed on Feb. 15, 2012, provisional application No. 61/600,011, filed on Feb. 17, 2012.

(51) Int. Cl.
*A61N 1/36* (2006.01)
*A61N 1/05* (2006.01)

(52) U.S. Cl.
CPC ............. *A61N 1/36* (2013.01); *A61N 1/0565* (2013.01); *A61N 1/36053* (2013.01); *A61N 1/36182* (2013.01)

(58) Field of Classification Search
CPC .................................. A61N 1/057; A61N 1/36
USPC ................ 607/116, 119, 125, 126, 127, 132; 600/373; 721/116, 119, 125, 126, 127, 721/132
See application file for complete search history.

(56) References Cited

U.S. PATENT DOCUMENTS

| 4,301,815 A | * 11/1981 | Doring .................... 607/126 |
| 4,519,404 A | * 5/1985 | Fleischhacker ........... 607/126 |
| 4,538,623 A | 9/1985 | Proctor et al. |

(Continued)

FOREIGN PATENT DOCUMENTS

| JP | 2002521154 A | 7/2002 |
| JP | 2002534137 A | 10/2002 |

(Continued)

OTHER PUBLICATIONS

International Preliminary Report on Patentability, Chapter II, issued in PCT/US2012/070958, dated Feb. 28, 2014, 8 pages.

(Continued)

*Primary Examiner* — Christopher A Flory
(74) *Attorney, Agent, or Firm* — Faegre Baker Daniels LLP

(57) ABSTRACT

An implantable cardiac rhythm management (CRM) system for directing stimulation energy toward a target tissue and away from unwanted tissues for providing an appropriate stimulation is provided by the present invention. The implantable cardiac rhythm management (CRM) system includes an implantable lead. The implantable lead includes a lead body and an electrically insulating member. The lead body includes at least one electrode extending substantially around the lead body. The electrically insulating member defines at least one window. At least one insulating member includes a protruding portion configured to urge at least one electrode toward the target tissue.

3 Claims, 28 Drawing Sheets

(56) References Cited

U.S. PATENT DOCUMENTS

| | | | |
|---|---|---|---|
| 4,796,643 A * | 1/1989 | Nakazawa et al. | 607/128 |
| 5,366,496 A * | 11/1994 | Dahl et al. | 607/132 |
| 5,991,668 A | 11/1999 | Leinders et al. | |
| 6,463,334 B1 * | 10/2002 | Flynn et al. | 607/127 |
| 6,912,423 B2 * | 6/2005 | Ley et al. | 607/37 |
| 7,184,841 B1 * | 2/2007 | Bodner et al. | 607/122 |
| 7,212,867 B2 | 5/2007 | Venrooij et al. | |
| 7,835,801 B1 | 11/2010 | Sundararajan et al. | |
| 2002/0072744 A1 * | 6/2002 | Harrington et al. | 606/41 |
| 2002/0183817 A1 | 12/2002 | Van Venrooij et al. | |
| 2003/0023294 A1 * | 1/2003 | Krall et al. | 607/122 |
| 2004/0093052 A1 * | 5/2004 | Westlund et al. | 607/116 |
| 2004/0204720 A1 * | 10/2004 | Harrington et al. | 606/119 |
| 2005/0131511 A1 * | 6/2005 | Westlund | 607/126 |
| 2005/0202703 A1 * | 9/2005 | Westlund et al. | 439/188 |
| 2006/0282144 A1 * | 12/2006 | Knapp et al. | 607/116 |
| 2007/0215163 A1 * | 9/2007 | Harrington et al. | 128/831 |
| 2007/0282412 A1 * | 12/2007 | Soltis et al. | 607/119 |
| 2007/0282414 A1 * | 12/2007 | Soltis et al. | 607/122 |
| 2007/0293922 A1 * | 12/2007 | Soltis et al. | 607/122 |
| 2007/0293923 A1 | 12/2007 | Soltis et al. | |
| 2008/0161871 A1 * | 7/2008 | Knapp et al. | 607/5 |
| 2008/0228251 A1 * | 9/2008 | Hill | 607/126 |
| 2008/0262588 A1 * | 10/2008 | Zarembo et al. | 607/127 |
| 2009/0318999 A1 * | 12/2009 | Hall | 607/37 |
| 2010/0036451 A1 | 2/2010 | Hoffer | |
| 2010/0331938 A1 | 12/2010 | Sommer et al. | |
| 2011/0301677 A1 * | 12/2011 | Hendricks et al. | 607/116 |
| 2013/0158640 A1 * | 6/2013 | Soltis et al. | 607/116 |

FOREIGN PATENT DOCUMENTS

| | | |
|---|---|---|
| JP | 2006504475 A | 2/2006 |
| JP | 2008080353 A | 4/2008 |
| WO | 199913941 A1 | 3/1999 |

OTHER PUBLICATIONS

International Search Report and Written Opinion issued in PCT/US2012/070958, dated Apr. 18, 2013, 14 pages.

* cited by examiner

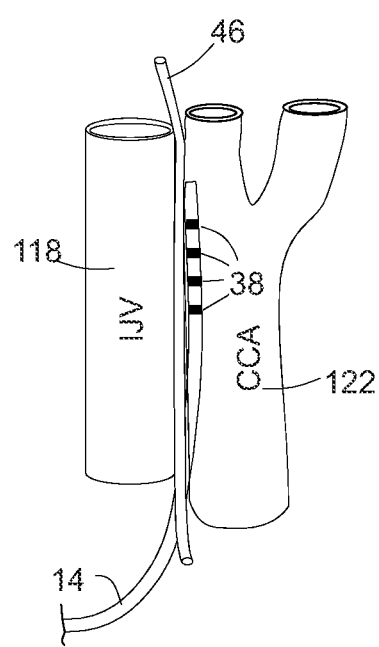 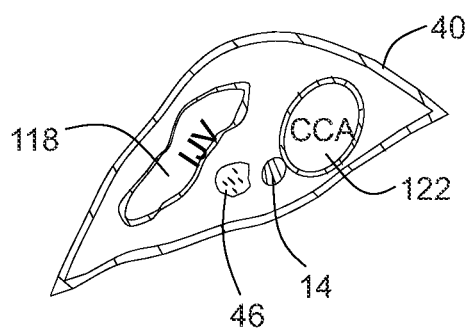
FIG. 3A
FIG. 3B

14

14

DIRECTIONAL FEATURES FOR IMPLANTABLE MEDICAL LEADS

CROSS-REFERENCE TO RELATED APPLICATIONS

This application claims the benefit under 35 U.S.C. § 119 of each of U.S. Provisional Patent Application No. 61/578,628, filed Dec. 21, 2011, entitled "SELECTIVE INSULATION FEATURE FOR IMPLANTABLE MEDICAL LEAD," U.S. Provisional Patent Application No. 61/599,060, filed Feb. 15, 2012, entitled "ROTATIONAL BIASING FEATURE FOR IMPLANTABLE MEDICAL LEAD," and U.S. Provisional Patent Application No. 61/600,011, filed Feb. 17, 2012, entitled "ROTATIONAL PROTRUSION FEATURE FOR ELECTRODE BIASING IN IMPLANTABLE MEDICAL LEAD," each of which is incorporated herein by reference in its entirety for all purposes.

BACKGROUND

Implantable medical leads are devices that deliver electrical stimulation from implantable devices to a target location within a body. Exemplary implantable devices are cardiac rhythm management (CRM) systems (e.g. pacemakers, defibrillators, and cardiac resynchronization therapy devices) and neurostimulation systems (e.g., spinal cord stimulation (SCS) systems and autonomic modulation therapy (AMT) systems). For CRM systems, implantable leads are typically advanced intravascularly to an implant location within a patient's heart, while in neurostimulation systems, such leads are typically positioned in the neck or limbs, pectoral region, epidural space of the spinal cord, or intramuscularly. Implantable leads may also be used to stimulate the autonomic nervous system (ANS), which regulates involuntary body functions such as heart rate, digestion, and respiratory rate. The ANS regulates autonomic balance which, in turn, impacts a variety of cardiac functions, including heart rate, heart rhythm, contractility, remodeling, inflammation and blood pressure. Precise placement of the implantable medical leads inside the body is important to ensure the leads deliver electrical stimulation to a target tissue without excessively stimulating other nearby tissues.

SUMMARY

In Example 1, an implantable medical lead for stimulating or sensing a target tissue and minimizing stimulation of a surrounding tissue includes a lead body having a proximal end portion, a distal end portion, and at least one electrode extending circumferentially around at least a portion of the lead body. An insulating sheath is disposed over at least a portion of the distal end portion of the lead body, the insulating sheath being configured to rotate about the lead body and having an exposure window adapted to electrically expose the at least one electrode to the target tissue. At least one protrusion extends radially outward from a portion of the insulating sheath at a location generally opposed to the exposure window, the protrusion adapted to urge the at least one electrode toward the target tissue upon rotation of the insulating sheath about the lead body such that a distance between the at least one electrode and the target tissue is less than a corresponding distance between the at least one electrode and a surrounding tissue.

Example 2 is the implantable medical lead of Example 1, wherein the protrusion is integrally formed with the insulating sheath. Example 3 is the implantable medical lead of Examples 1 or 2, wherein the insulating sheath comprises an inner insulating member and an outer insulating member having a compartment, and further wherein the protrusion is disposed on the inner insulating member and is configured to extend at least partially through the compartment. Example 4 is the implantable medical lead of any of Examples 1-3, wherein rotation of the inner insulating member with respect to the outer insulating member is limited by a contact between the protrusion and an edge of the compartment. Example 5 is the implantable medical lead of any of Examples 1-4, wherein the lead body includes a plurality of electrodes and the insulating sheath includes a plurality of protrusions, and further wherein each protrusion is disposed at a location along a length of the insulating sheath aligned with a location of a corresponding electrode.

Example 6 is the implantable medical lead of any of Examples 1-5, wherein the protrusion extends circumferentially around the insulating sheath through an angle of between about 25 and about 120 degrees. Example 7 is the implantable medical lead of any of Examples 1-6, wherein the protrusion is a separate structure coupled to the insulating sheath and configured to allow attachment during delivery of the lead. Example 8 is the implantable medical lead of any of Examples 1-7, wherein the protrusion is made from an insulating material and is configured to insulate the surrounding tissue from electrical stimulation delivered by the at least one electrode. Example 9 is the implantable medical lead of any of Examples 1-8, wherein the exposure window is selected from the group consisting of a physical window and an electrically permeable window. Example 10 is the implantable medical lead of any of Examples 1-9, wherein the protrusion extends radially outward from the insulating sheath a distance of between about 1 mm and about 5 mm.

In Example 11, an implantable medical lead for stimulating or sensing a target tissue and minimizing stimulation of a surrounding tissue includes a lead body including a proximal end portion, a distal end portion, and a plurality of spaced-apart electrodes extending circumferentially around at least a portion of the lead body. An insulating sheath is disposed over at least a portion of the distal end portion of the lead body, the insulating sheath being configured to rotate about the lead body and having a plurality of exposure windows adapted to electrically expose at least one of the plurality of electrodes to the target tissue. A plurality of insulating protrusions extend radially outward from a portion of the insulating sheath at a location generally opposed to a corresponding exposure window. The protrusions are adapted to urge a corresponding exposure window towards the target tissue upon rotation of the insulating sheath about the lead body, such that a distance between the corresponding exposure window and the target tissue is less than a corresponding distance between the corresponding exposure window and a surrounding tissue.

Example 12 is the implantable medical lead of claim 11, wherein each of the plurality of insulating protrusions extends circumferentially around the insulating sheath through an angle of between about 25 and about 120 degrees. Example 13 is the implantable medical lead of Examples 11 or 12, wherein each of the exposure windows is selected from the group consisting of a physical window and an electrically permeable window. Example 14 is the implantable medical lead of any of Examples 11-13, wherein the protrusion is integrally formed with the insulating sheath. Example 14 is the implantable medical lead of any of examples 11-13, wherein the plurality of insulating protrusions are configured to insulate the surrounding tissue from electrical stimulation delivered by the plurality of spaced-apart electrodes. Example 15 is the implantable medical lead of any of examples 11-14, wherein the insulating sheath comprises an inner insulating member and an outer insulating member having a compartment, and further wherein the protrusion is disposed on the inner insulating member and is configured to extend at least partially through the compartment.

In Example 17, a method of providing electrical stimulation to a target tissue and minimizing electrical stimulation of a surrounding tissue, includes providing a lead body including a proximal end portion, a distal end portion, and at least one electrode extending circumferentially around at least a portion of the lead body. The lead body has an insulating sheath disposed over at least a portion of the distal end portion of the lead body. The insulating sheath has an exposure window adapted to electrically expose the at least one electrode to the target tissue. The insulating sheath further has at least one protrusion extending radially outward from a portion of the insulating sheath at a location generally opposed to the exposure window. The protrusion is adapted to urge the at least one electrode toward the target tissue upon rotation of the insulating sheath about the lead body. The method further includes advancing the distal end portion of the lead body such that at least one electrode is disposed at a location near the target tissue, and rotating the insulating sheath to adjust a position of the protrusion such that the protrusion urges the at least one electrode towards the target tissue and away from the surrounding tissue.

Example 16 is the method of Example 17, further comprising stimulating the target tissue with the at least one electrode. Example 19 is the method of Examples 17 or 18, further comprising attaching the protrusion to the insulating sheath prior to advancing the distal end portion of the lead body to a location near the target tissue. Example 20 is the method of any of Examples 17-19, wherein the target tissue is the vagus nerve and the surrounding tissue includes a muscle adjacent the vagus nerve, and further wherein the rotating step urges the at least one electrode towards the vagus nerve and away from the muscle adjacent the vagus nerve.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 3A-3B are schematic views of a carotid sheath including the internal jugular vein, the common carotid artery, and the vagus nerve.

Figure 1:
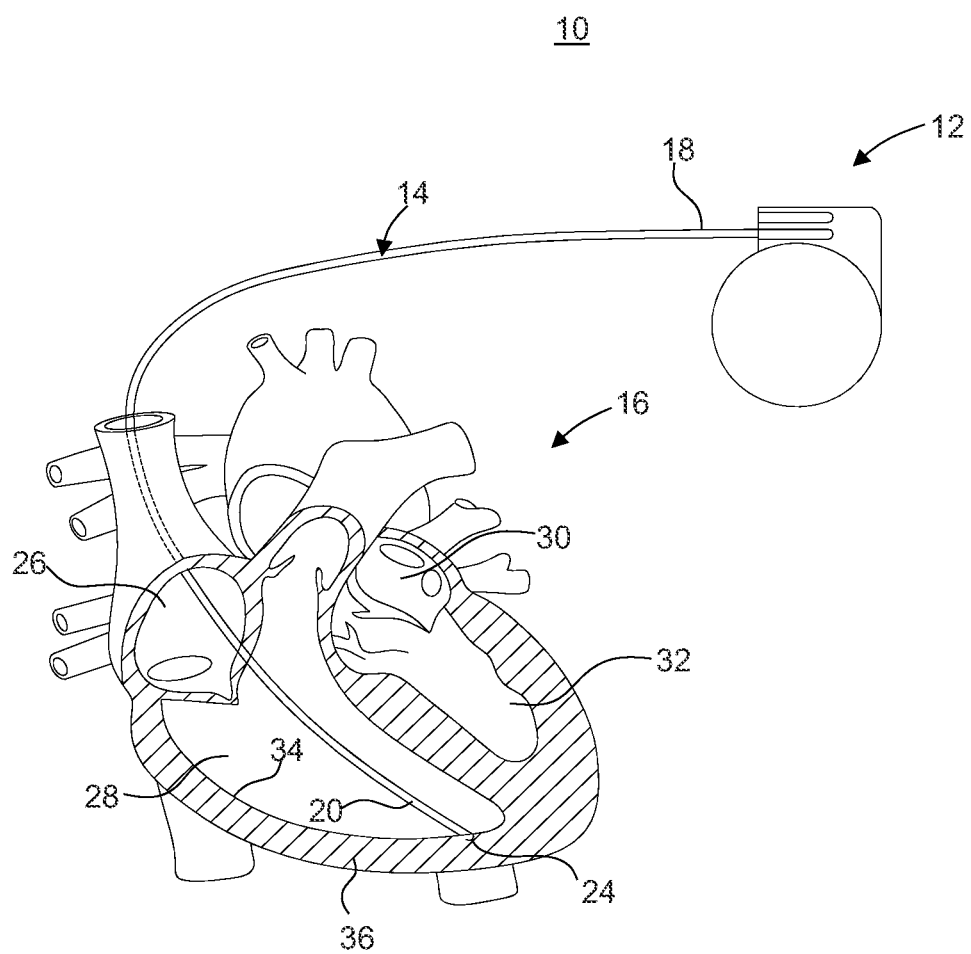
FIG. 1 is a schematic view of a cardiac rhythm management (CRM) system, according to various embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an implantable cardiac rhythm management (CRM) system 10. As shown, the system 10 includes a pulse generator 12 and an implantable lead 14, which extends from a proximal end portion 18 to a distal end portion 20. As shown in FIG. 1, the heart 16 includes a right atrium 26, a right ventricle 28, a left atrium 30 and a left ventricle 32. The heart 16 further includes an endocardium 34 covering the myocardium 36. In some embodiments, as illustrated, a fixation helix 24, located at the distal end portion 20 of the lead 14, penetrates through the endocardium 34 and is embedded within the myocardium 36. In some embodiments, the fixation helix 24 is electrically active and thus operates as a helical electrode for sensing the electrical activity of the heart 16 and/or applying a stimulating pulse to the right ventricle 28. In one embodiment, the CRM system 10 includes a plurality of leads 14. For example, it may include a first lead 14 adapted to convey electrical signals between the pulse generator 12 and the right ventricle 28 and a second lead (not shown) adapted to convey electrical signals between the pulse generator 12 and the right atrium 26 or coronary veins (not shown).

Figure 2:
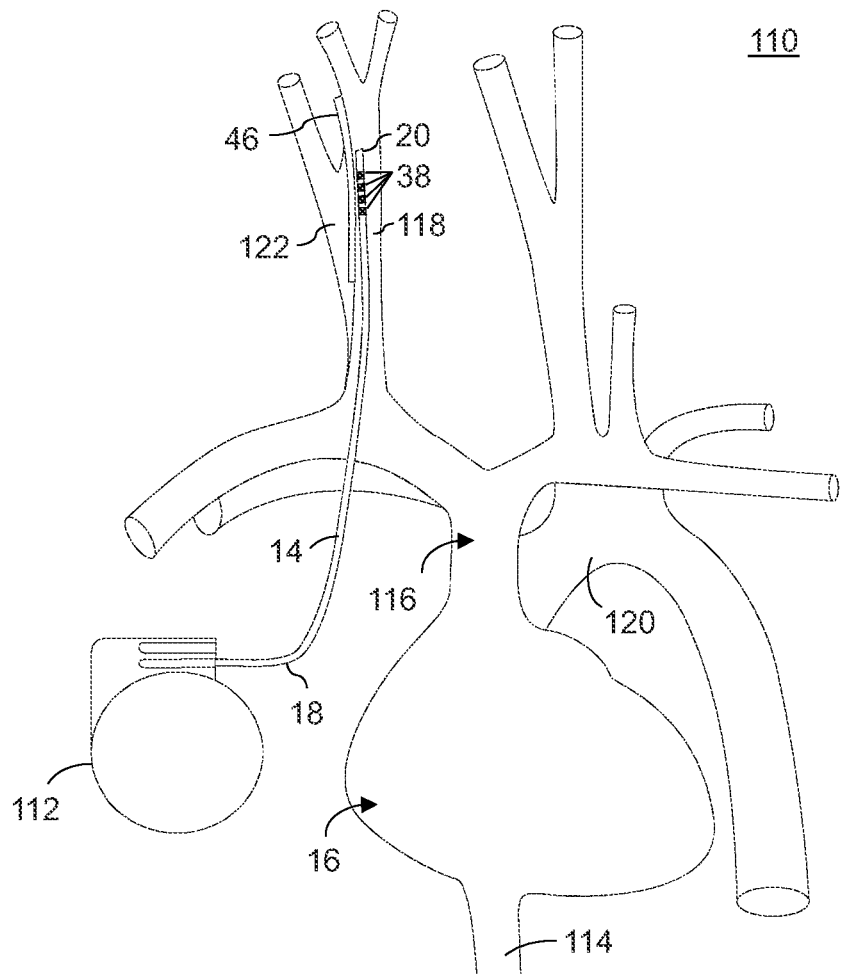
FIG. 2 is a schematic view of an autonomic modulation therapy (AMT) system, according to various embodiments.

FIG. 2 is a schematic view of a representative implantable autonomic modulation therapy (AMT) system 110. As shown in FIG. 2, the AMT system 110 includes an implantable pulse generator 112, which generates electrical stimulation pulses, and a lead 14 extending from the pulse generator 112 to a desired stimulation site. As further shown in FIG. 2, the inferior vena cava (IVC) 114 and superior vena cava (SVC) 116 extend from the right atrium of the heart 16. The SVC 116 is coupled to the inferior jugular vein (IJV) 118. The aorta 120 extends from the left atrium of the heart 16. The aorta 120 is coupled to the common carotid artery (CCA) 122. The IJV 118 and the CCA 122 extend adjacent one another through a portion of the neck region. As shown, the vagus nerve 46 also extends through the neck region in a location near the IJV 118 and the CCA 122. Furthermore each of these structures is disposed within fibrous connective tissue known as the carotid sheath. The lead 14 has a proximal end portion 18 and a distal end portion 20 and includes an electrode or plurality of electrodes 38 at or near the distal end portion 20.

FIGS. 3A and 3B show an exemplary anatomical location for implantation of the AMT system 110. In particular, these figures show structure found in a neck region and within the carotid sheath 40. FIG. 3A is a perspective view of this anatomical region and FIG. 3B is sectional view of the carotid sheath 40. As shown, the implantable lead 14 may be positioned within the carotid sheath 40 with the electrodes 38 located at or near the vagus nerve 46, the CCA 122 and the IJV 118 (along with the surrounding muscles and other tissues).

Figure 4A:
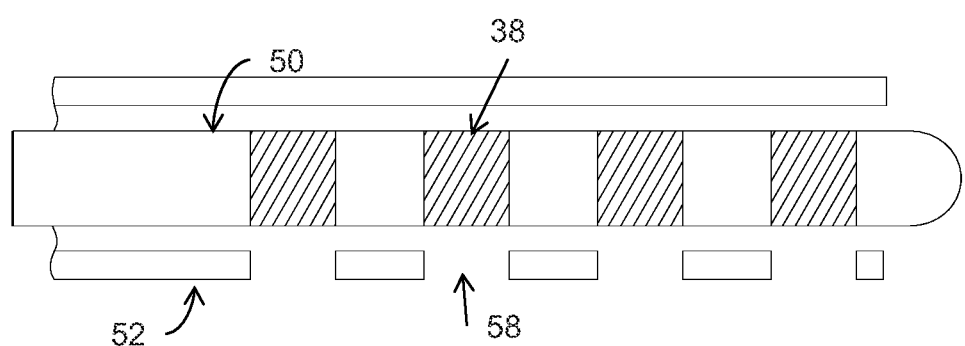
FIGS. 4A-4B are schematic views of an implantable lead having a sheath with open windows, according to various embodiments.
Figure 4B:
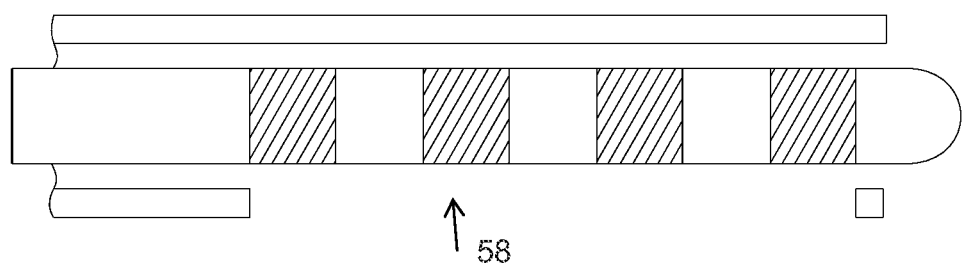

FIGS. 4A and 4B show a distal portion of an implantable lead 14 for use delivering stimulation energy to a desired site in an implantable system such as, for example, the CRM system 10 or the AMT system 110, according to various embodiments. The implantable lead 14 may be implanted in numerous locations including, for example, near the vagus nerve, the peripheral nerves, the spinal cord, or the heart. As shown, the distal portion of the implantable lead 14 includes a lead body 50 and an electrically insulating member (or sheath) 52. The lead body 50 includes one or more electrodes 38 extending partially or substantially around the lead body 50. In some embodiments, the lead body 50 includes an array of electrodes or a plurality of electrodes. As shown in FIGS. 4A and 4B, the lead body 50 includes four such electrodes 38 disposed around an outer periphery of the lead body and spaced apart along a longitudinal axis. In other embodiments, any other number of electrodes can be disposed over the lead body.

According to various embodiments, the electrodes extend different radial amounts around the lead body. For example, in some embodiments, at least one electrode is disposed around the lead body such that it covers a radial surface extending entirely (i.e., 360 degrees) around the lead body. In other embodiments, each electrode may extend around distinct radial locations (or arcs), such that the electrodes together extend entirely around the lead body. For example, the electrodes may include a first electrode disposed around the lead body such that it covers a radial surface over 0 to 90 degrees around the lead body defined as a first radial quadrant, a second electrode disposed around the lead body such that it covers a radial surface over 90 to 180 degrees around the lead body defined as a second radial quadrant, a third electrode disposed around the lead body such that it covers a radial surface over 180 to 270 degrees around the lead body defined as a third radial quadrant and a fourth electrode disposed around the lead body such that it covers a radial surface over 270 to 360 degrees around the lead body defined as a fourth radial quadrant. In these embodiments, each of the electrodes may be disposed at a different longitudinal location along the lead body, or one or more of the electrodes may be disposed at the same longitudinal location along the lead body.

In other embodiments, the electrodes may collectively extend around less than the entirety (i.e., 360 degrees) of the lead body. In these embodiments, for example, a first electrode may cover 0 to 90 degrees, a second electrode may cover 90 to 180 degrees, a third electrode may cover 0 to 90 degrees and a fourth electrode may cover 90 to 180 degrees. Furthermore, in various embodiments, the lead body may include fewer or more than four electrodes. In further embodiments, the electrodes may overlap as they extend radially around or about the surface of the lead body. For example, a first electrode may cover 0 to 90 degrees, a second electrode may cover 45 to 135 degrees, a third electrode may cover 90 to 180 degrees, and a fourth electrode may cover 135 to 225 degrees. In these embodiments, additional electrodes may also be added to cover additional radial locations around the circumference of the lead body.

The lead body 50 may be made from any flexible, biocompatible material suitable for lead construction. In various embodiments, the lead body 50 is made from a flexible, electrically insulative material, such as silicone rubber or polyurethane. In various embodiments, different segments of lead body 50 may be made from different materials to tailor the lead body characteristics to its intended clinical and operating environments. In some embodiments, the proximal and distal portions of the lead body 50 are made from different materials selected to provide the desired functionalities.

As further shown in FIGS. 4A and 4B, the electrically insulating member or sheath 52 extends axially over a distal portion of the lead body 50 that includes the one or more electrodes 38. The insulating sheath 52 may be made using a flexible polymer material with sufficient dielectric properties to adequately electrically isolate or insulate the electrodes 38. The insulating sheath 52 may be made from a thin-walled tube with sufficient mechanical properties for manipulation. According to various embodiments, the sheath 52 is made from any one or more of the following: silicone, polyurethane, polytetrafluoroethylene (PTFE), and ethylene tetrafluoroethylene (ETFE). In various embodiments, the sheath 52 is reinforced with, for example, a stainless steel braiding. In various embodiments, the electrically insulating member or sheath 52 may include a pre-defined shape, for example, helical S-shape, curved shape, or any other shape.

The insulating member 52 defines one or more windows 58. The electrically insulating member 52 is configured to be translated (i.e., moved axially) along the longitudinal axis of the lead body, rotated around the lead body, or both translated and rotated, such that in a first defined radial position, a first portion of the at least one electrode 38 is exposed through the at least one window 58 and a second portion of the at least one electrode 38 is covered by the electrically insulating member 52. In this way, an operator (e.g., a physician) may expose a portion of the electrode 38 best suited to stimulate a desired target site (e.g., the vagus nerve), while simultaneously covering other portions of the electrode 38 to prevent (or reduce) undesired stimulation of other tissues. According to some embodiments, as shown in FIG. 4A, the insulating sheath 52 includes multiple windows. In some embodiments, these windows are spaced longitudinally along the sheath with the same (or substantially the same) spacing as that between the electrodes 38, such that each window corresponds to a specific electrode. According to other embodiments, as shown for example in FIG. 4B, the insulating sheath 52 includes one window that is sized and shaped to correspond to more than one (e.g., two, three, or all) of the electrodes. According to some embodiments, for example the embodiments shown in FIGS. 4A and 4B, the windows are open sections where the insulating material has been removed to create a mechanical opening.

Figure 5A:
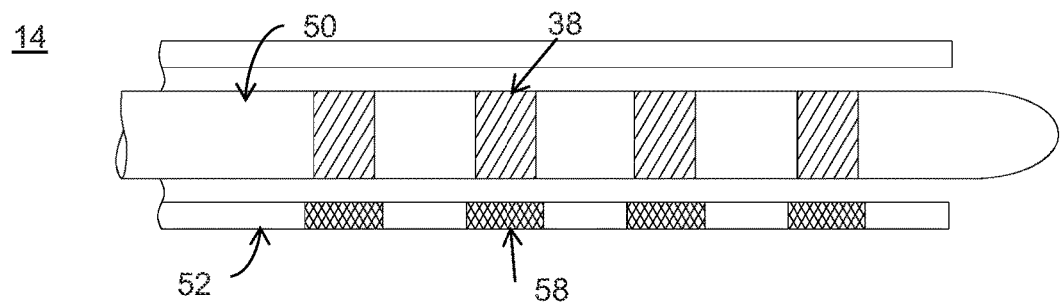
FIGS. 5A-5B are schematic views of an implantable lead having a sheath with electrically permeable windows, according to various embodiments.
Figure 5B:
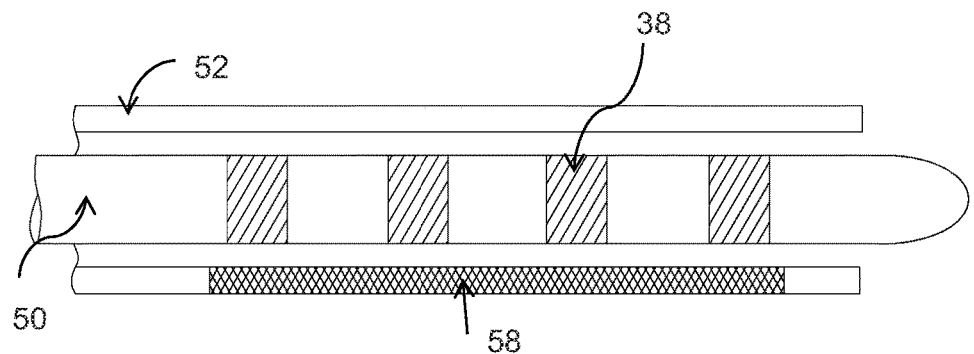

According to other embodiments, for example as shown in FIGS. 5A and 5B, the window 58 can be an electrically conductive or electrically permeable area formed within the lead body material. This electrically permeable window may be formed for example from any conductive polymeric material, including, for example, expanded polytetrafluoroethylene (ePTFE). In various embodiments, the insulating sheath 52 includes multiple windows comprised of a combination of mechanical openings and electrically conductive portions. In some embodiments, the windows are disposed at the same radial locations along the lead body 50 in a linear manner, such that all of the windows are generally centered along the same line. In other embodiments, the windows are disposed at distinct or overlapping radial locations along the lead body.

Figure 6A:
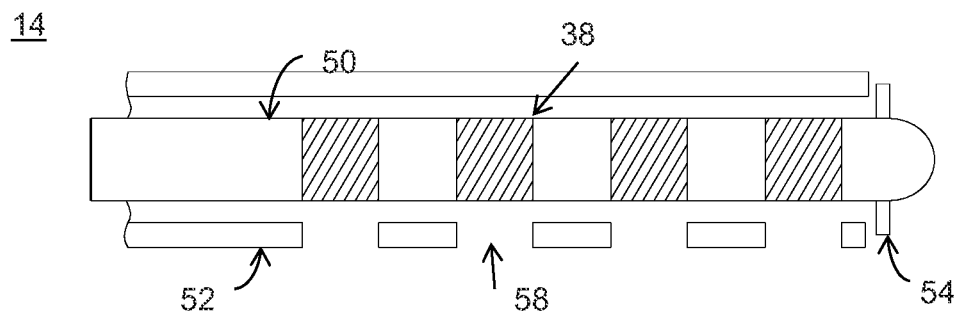
FIGS. 6A-6B are schematic views of an implantable lead having stopping members, according to various embodiments.
Figure 6B:
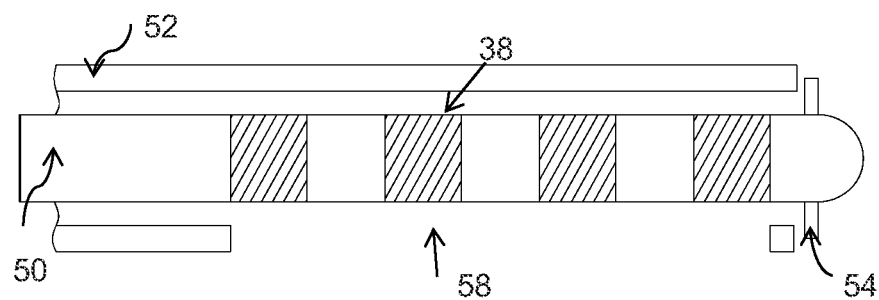

FIGS. 6A and 6B are schematic views of a distal portion of the implantable lead 14 for use in an implantable system such as the CRM system 10 or the AMT system 110. As shown, in these embodiments, the implantable lead 14 includes a stopping member 54 coupled to the lead body 50. In the illustrated embodiments, the stopping member 54 resides at or near the distal end of the lead body 50. In various other embodiments, the stopping member 54 may reside at any other location along the lead body 50. As shown, the stopping member is disposed at a location along the lead body that facilitates alignment of the window (or windows) 58 on the insulating sheath 52 with the electrode (or electrodes) 38. This feature would allow, for example, a user (e.g., a physician) to advance the insulating sheath 52 distally over the lead body 50 until the sheath 52 makes contact with the stopping member 54. Upon making such contact, the physician knows that the sheath 52 is disposed at a longitudinal location along the lead body 50, where the windows 58 are aligned (or substantially aligned) with the electrodes 38.

Figure 7A:
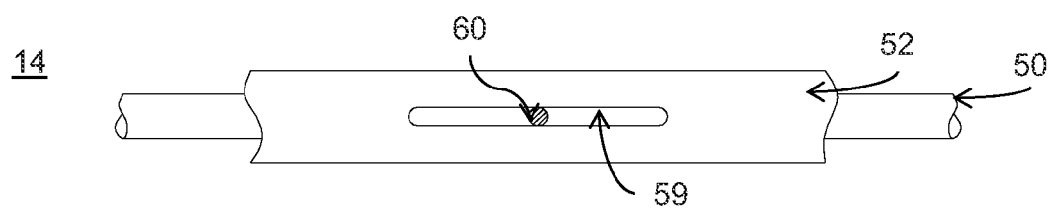
FIG. 7A is a schematic view and FIG. 7B is a cross-sectional view of an implantable lead with a stopping member, according to various embodiments.
Figure 7B:
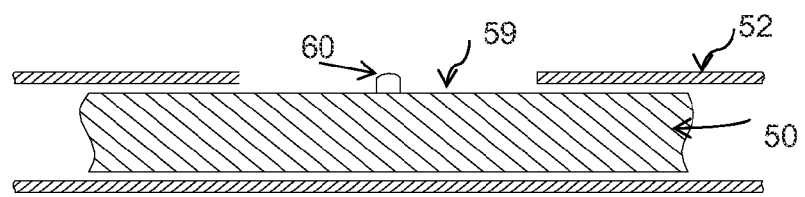
Figure 8:
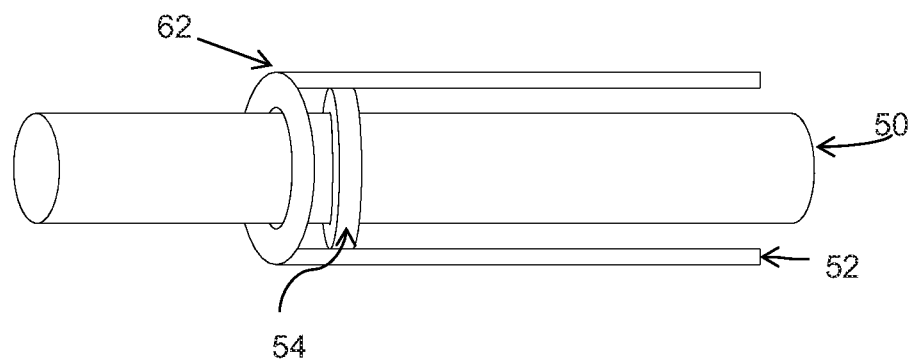
FIG. 8 is a perspective view of an implantable lead with a stopping member, according to various embodiments.

Several other types of stopping members may be provided on the lead body, such as those shown for example in FIGS. 7A, 7B, and 8. FIGS. 7A and 7B are perspective and sectional views of an implantable lead 14 having a pin or protrusion 60 configured to function as a stopping member. As shown in FIG. 7A, the sheath 52 includes a groove or slot 59 sized to accept the protrusion 60. The slot 59 and protrusion 60 may be located at any longitudinal position along the sheath 52 and lead body 50. The slot 59 is selected to have a length sufficient to allow a desired amount of longitudinal movement of the sheath along the lead body. As shown in FIG. 7B, the protrusion 60 is coupled to the lead body 50 such that one end portion of the pin 60 extends radially outward from the lead body 50 a sufficient distance to engage the slot 59. The outward extended portion of the pin 60 is configured to be received and slid along the length of the slot 59 such that the movement is restricted at either of the two end portions of the slot provided in the insulating member 52. In addition, the pin 60 further resists or prevents rotational movement of the sheath 52 about the lead body 50.

FIG. 8 is a perspective view of an implantable lead 14, including features for controlling movement of a sheath 52 along a lead body 50. As shown, the lead body 50 includes a protrusion or step 54 extending radially outward from the lead body 50, and the sheath 52 includes an inwardly extending ring 62. As shown, the step 54 is adapted to mechanically contact the ring 62 to resist or prevent longitudinal (i.e., axial) motion of the sheath along the lead body. In various embodiments, the sheath 52 is configured to extend over the step 54, such that the step 54 is located inside the sheath 52. The step 54 and the ring 62, according to some embodiments, are located on a proximal portion of the lead body 50 and sheath 52, respectively, such that these structures act as a stop to distal motion. In other words, as a user advances the sheath 52 toward a distal end of the lead body, at the location where the step 54 and the ring 62 make contact, further distal movement of the sheath is resisted or prevented. Again, the location of the step 54 may be selected to facilitate the desired alignment of windows in the sheath with electrodes on the lead body.

Figure 9A:
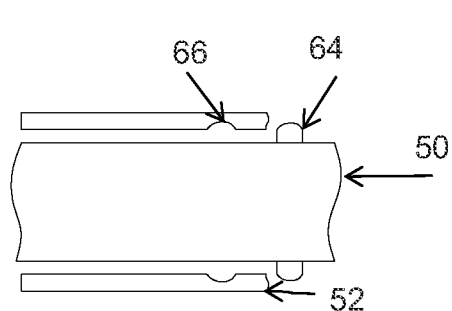
FIGS. 9A and 9B are schematic views of an implantable lead with a locking member, according to various embodiments.
Figure 9B:
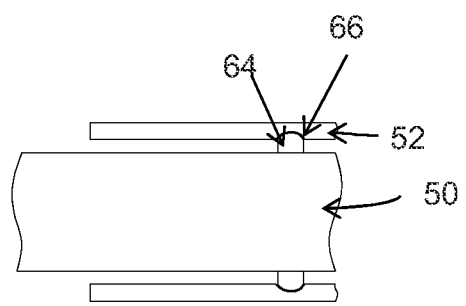

FIGS. 9 and 10 show further structures for positioning and/or securing the sheath 52 along the lead body 50 of the lead 14. As shown in FIGS. 9A and 9B, the lead body 50 includes a radially extending protrusion or nub 64, which is adapted to mate with or couple to a recess or groove 66 in the sheath 52. FIG. 9A illustrates a configuration where the nub 64 is disengaged from the recess 66, and FIG. 9B illustrates a configuration where the nub 64 is engaged within the recess 66. These features may be located at any longitudinal location along the lead body 50 and the sheath 52 and disposed at appropriate locations to align or substantially align any windows located in the sheath 52 with electrodes located along the lead body 50.

Figure 10A:
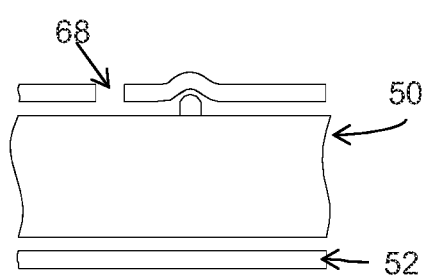
FIGS. 10A and 10B are schematic views of an implantable lead with a locking member, according to various embodiments.
Figure 10B:
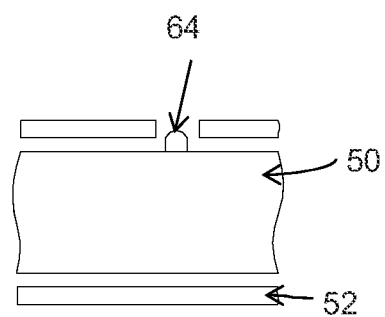

FIGS. 10A and 10B show other embodiments where the recess 66 is replaced by an aperture 68 such that the nub 64 is configured to engage with the aperture 68 provided in the sheath 52 of the lead 14. FIG. 10A illustrates a configuration where the nub 64 is disengaged from the aperture 68 and FIG. 10B illustrates a configuration where the nub 64 is engaged with the aperture 68. These features may be located at any longitudinal location along the lead body 50 and the sheath 52 and disposed at appropriate locations to align or substantially align any windows located in the sheath 52 with electrodes located along the lead body 50.

Figures 11A, 11B:
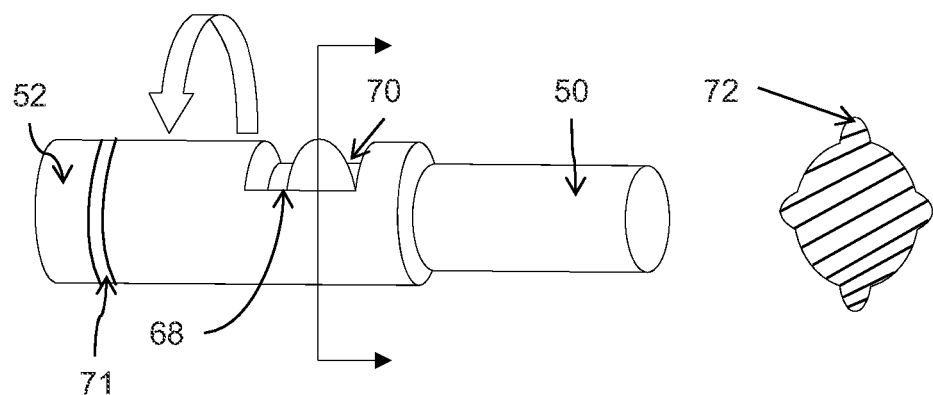
FIG. 11A is a perspective view and FIG. 11B is a cross-sectional view of an implantable lead with a locking member, according to various embodiments.

FIGS. 11A and 11B show embodiments of the implantable lead 14 including a radial locking member 70. The radial locking member 70 is configured to lock the electrically insulating member 52 over the lead body 50 at a plurality of radial positions around the lead body 50. In this particular embodiment, the electrically insulating member 52 further includes an aperture 68. Further, the radial locking member 70 includes a plurality of protrusions such as nubs 72 configured to engage with the opening 68. At one locking position, only one of the nubs 72 is in engaged configuration with the opening 68. For example, at a first radial position, a first nub is engaged with the opening 68 and a second nub is engaged with the opening 68 at a second radial position. FIG. 11A illustrates a perspective view of a configuration where one of the plurality of nubs 72 is engaged with the opening 68. FIG. 11B illustrates a cross-sectional view of the lead body 50 having nubs 72. In the illustrated embodiment, four such nubs 72 are shown. In various other embodiments, different number of nubs 72 can be employed in the lead body design. By increasing the number of nubs 72, the resolution of the radial adjustment of the sheath 52 around the lead body 50 may be increased, so as to give the user more options to best direct stimulation energy from the electrodes towards a desired target tissue. In some embodiments, the sheath 52 may also include a suture sleeve or suture groove 71 adapted to accept a suture for fixing the position of the sheath 52 with respect to the lead body 50. In some embodiments, the suture groove 71 is integrated with the electrically insulating member 52. In other embodiments, a suture sleeve is provided as a separate member from the sheath 52.

Figure 12A:
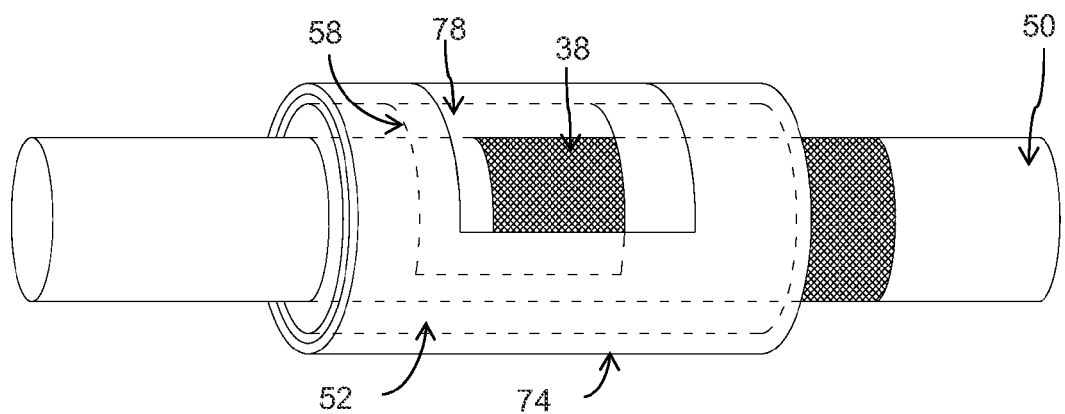
FIGS. 12A-12D are perspective views of an implantable lead having multiple electrically insulating members or sheaths, according to various embodiments.

FIG. 12A is a perspective view of the implantable lead 14, for use in an implantable system such as the CRM system 10 or the AMT system 110. In this particular embodiment, the implantable lead 14 includes, in addition to the insulating member or sheath 52, a second electrically insulating member or sheath 74. Similar to the sheath 52, which has one or more windows 58, the sheath 74 also defines one or more windows 78. Such an embodiment allows for increased exposure options by allowing the user to adjust both the sheath 52 and the sheath 74 to provide for an overlap of the corresponding windows 58, 78.

Figure 12B:
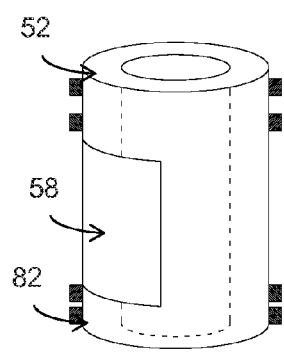
Figure 12C:
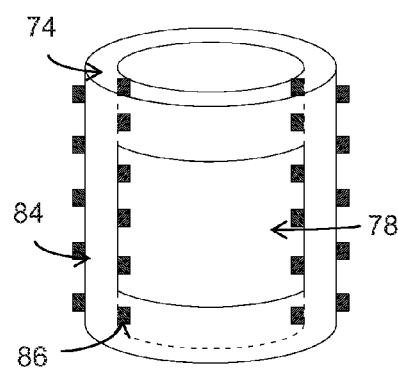
Figure 12D:
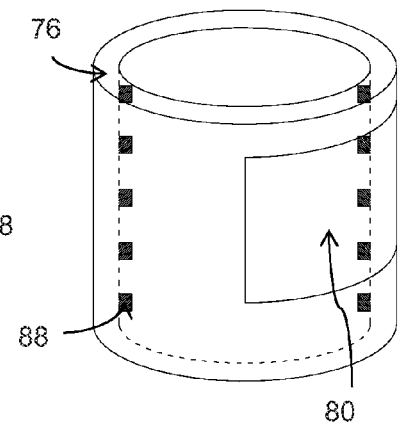

FIGS. 12B, 12C, and 12D are perspective views showing embodiments include multiple three electrical insulating members or sheaths. FIG. 12B shows a first sheath 52 including a first window 58, FIG. 12C shows a second sheath 74 including a second window 78, and FIG. 12D shows a third sheath 76 including a third window 80. As further shown, these embodiments including corresponding threads 82, 84, 86, 88 for allowing adjustment of each of the sheaths 52, 74, 76 with respect to each other. When assembled to form a lead 14, the sheath 74 extends axially end-to-end over the sheath 52. In various embodiments, the sheath 74 may extend axially over the sheath 52 up to a certain portion of the length of the sheath 52. Similarly, in some embodiments, the sheath 76 may also extend axially end-to-end over the sheath 74. Further, in some other embodiments, the sheath 76 may extend axially over the sheath 74 up to a certain portion of the length of the sheath 74. While the illustrated embodiment describes use of three sheaths 52, 74, and 76. In various embodiments, the lead 14 includes more or fewer than three sheaths.

As shown in FIG. 12B, the first sheath 52 includes a set of outwardly extending threads 82, which are adapted to mate with a set of inwardly extending threads 86 on the second sheath 74. These threads allow adjustment of both the longitudinal and or rotational alignment of the first sheath 52 with the second sheath 74. As further shown, the electrically insulating member 74 further includes a set of outwardly extending threads 84, which are adapted to mate with a set of inwardly extending threads 88 located on the third sheath 76. This configuration allows the user (e.g., a physician) to control the relative longitudinal and rotational orientations of each of the sheath 52, 74, 76, which in turn allows for control of the relative orientations of each of the corresponding windows 58, 78, 80. According to other embodiments, the threads 82, 86 are replaced with alternative structures (e.g., guiding posts) for effecting simultaneous and controlled axial and radial motion.

Figure 13:
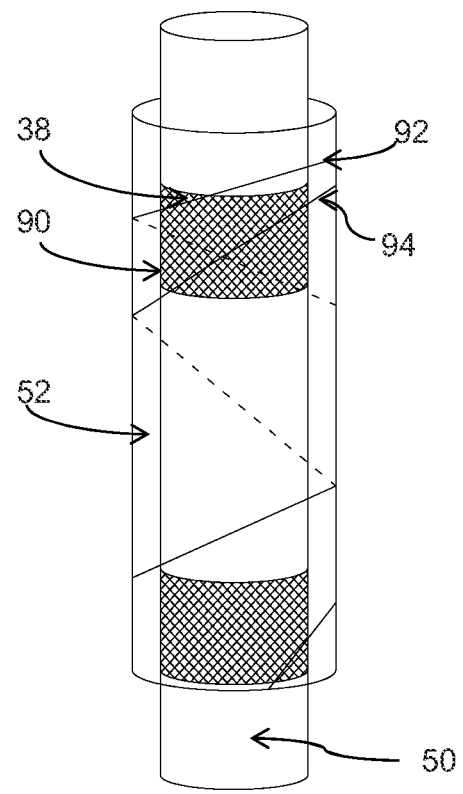
FIGS. 13 and 14 are perspective views implantable leads, according to various embodiments.

FIG. 13 is a perspective view of the implantable lead 14 for use in an implantable system such as the CRM system 10 or the AMT system 110. As shown, the electrically insulating member or sheath 52, extending axially over a portion of the lead body 50, defines a generally helical shaped window 90. The helical window 90 includes a first helix edge 92 and a second helix edge 94. While the helix edges 92, 94 are shows as non-parallel, in other embodiments, the edges are parallel. The helix edges 92, 94 define a helical path that creates the helical shaped window 90. The helical shaped window 90 is configured to expose an area of the electrode 38 that is dependent upon at least one of a radial position and an axial position of the electrically insulating member 52 over the lead body 50. In this embodiment, the user (e.g., a physician) may vary the exposure of the electrode 38 on the lead body 52. In various embodiments, the sheath 52 and lead body 50 may includes various stopping members of control features to provide for further control and adjustment of the helical window 90 with respect to the electrodes 38.

Figure 14:
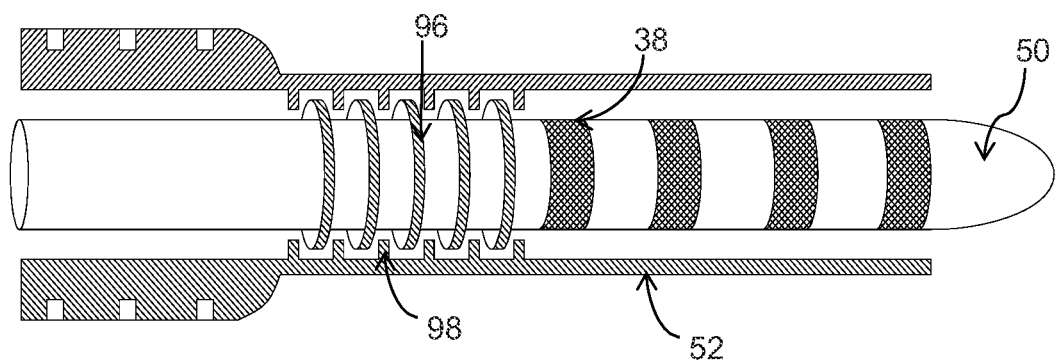

FIG. 14 is a perspective view of the implantable lead 14 for use in an implantable system such as the CRM system 10 or the AMT system 110. As shown, the lead body 50 includes a series of outward protrusions 96 disposed in a series of grooves 98 located in an inner surface of the sheath 52. The series of outward protrusions 96 are configured to engage with the series of grooves 98 to assist the user in controlling a radial adjustment and an axial adjustment of the sheath 52 over the lead body 50. The protrusions and grooves are configures to provide a resistance to axial motion, rotational motion, or both, so as to allow the user to adjust the axial and rotations positions in a controlled manner. According to various embodiments, the protrusions 96 and grooves 98 are configured as mating threads to allow controlled axial and rotational adjustment.

Figure 15A:
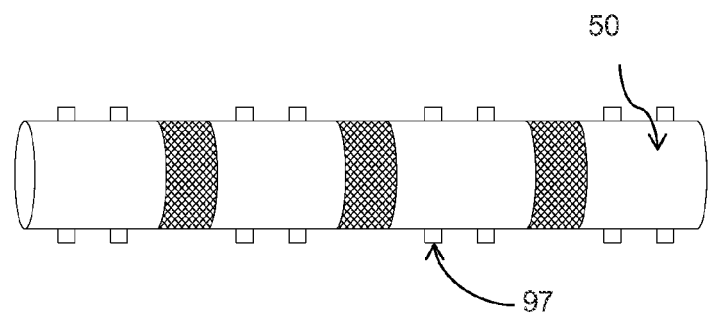
FIGS. 15A, 15B and 15C are perspective views of a lead body, an inside view of a portion of an electrically insulating member and an implantable lead, respectively, according to various embodiments.
Figure 15B:
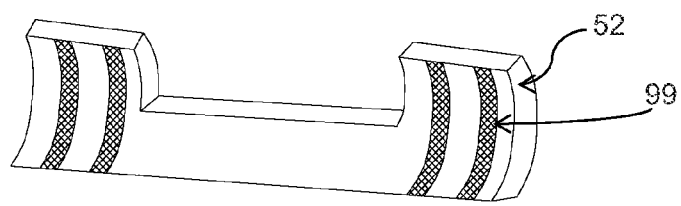
Figure 15C:
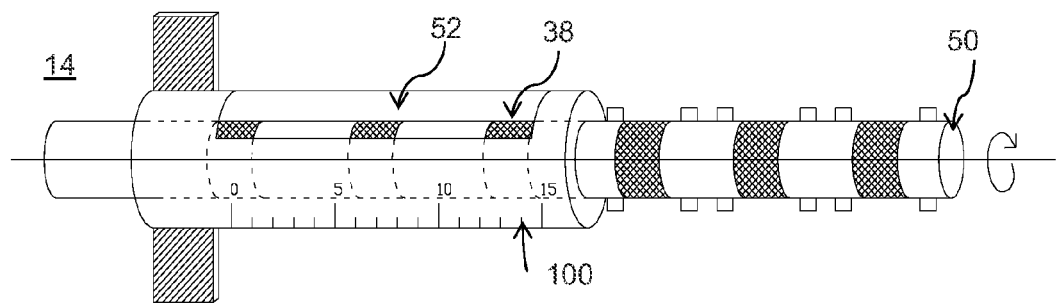

FIG. 15A is a perspective view of an implantable lead 14 for use in an implantable system such as the CRM system 10 or the AMT system 110. In this particular embodiment, the lead body 50 includes a first threaded portion 97 over its outer diameter end-to-end between the proximal end portion 18 and the distal end portion 20 of the lead body 50. The sheath 52 includes a second threaded portion 99 over its inner diameter at distinct locations, as shown in FIG. 15B. In other embodiments, the second threaded portion 99 can be provided over an entire length of the sheath 52. The first threaded portion 97 is configured to engage with the second threaded portion 99 to allow at least one radial adjustment and an axial adjustment of the sheath 52 over the lead body 50, as shown in FIG. 15C. In one embodiment, the first threaded portion 97 is a male thread and the second threaded portion 99 is a female thread. In various embodiments, the first threaded portion 97 is a female thread and the second threaded portion 99 is a male thread.

In accordance with some embodiments, the sheath 52 may further include a radio opaque marker or scale 100. The radio opaque marker 100 is configured to show a radial position and an axial position of the sheath 52 with respect to the at least one electrode 38. The radio opaque marker 100 is further configured to facilitate in adjustment of the radial and axial position of the sheath 52 over the lead body 50 and to achieve a desired radial and axial placement of the sheath 52 over the lead body 50.

Figure 16:
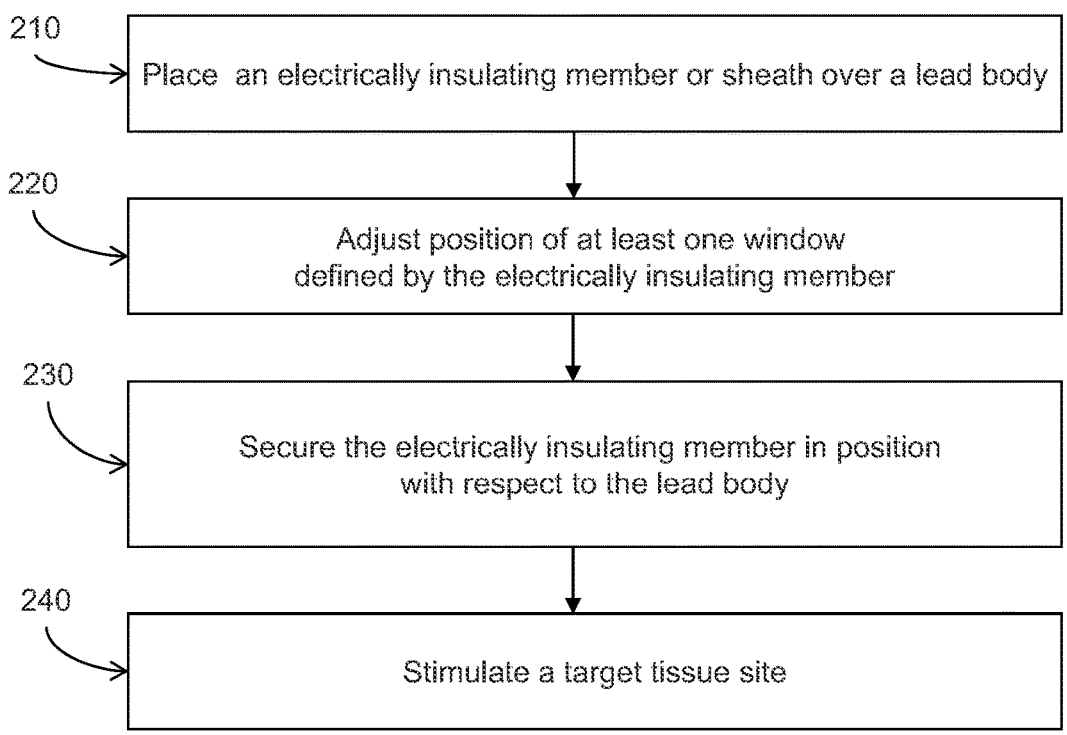
FIG. 16 is a flowchart showing a method of providing electrical stimulation at a tissue site, according to various embodiments.

FIG. 16 is a flow chart illustrating a method 200 for providing electric stimulation at a tissue site using an implantable medical lead. The method 200 may be used with any implantable medical lead in a number of various applications, including for example in a CRM system or an AMT system. The method is useful to allow a user (e.g., a physician) to direct stimulation toward a desired tissue sites (e.g., the vagal nerve) while also minimizing or preventing stimulation of undesired tissue sites (e.g., surrounding tissues). In various embodiments, the desired tissue may be other nerves and the undesired tissue may be other tissues surrounding these nerves.

The method 200 includes placing an electrically insulating member or sheath over an implantable lead body, the electrically insulating member defining at least one window that exposes a first portion of at least one electrode on the lead body when in a first position over the lead body (block 210). According to some embodiments, the lead body 50 is first advanced towards a target site and subsequently, the sleeve or sheath 52 is inserted over the lead body. According to other embodiments, the sleeve or sheath 52 is first placed over the lead body 50 and then the lead body and sleeve are advanced together to the target site. The sheath 52 is configured to selectively insulate the electrode 38 so as to effectively direct stimulation energy from the electrode 38 towards the target tissue and also to reduced or minimize stimulation of tissues adjacent to or surrounding the target tissues.

After the lead is placed in the desired location near the target tissue, the user (e.g., a physician) manipulates the sheath to adjust a radial orientation, a longitudinal position, or both, with respect to the lead body and the electrodes, so as to effectively adjust the size and shape of the exposed portion of the electrode (block 220). This adjustment may be performed either before or after the lead is advanced to a location near the target tissue. In those embodiments where this adjustment occurs after advancing the lead to a site at or near the target tissue, the radial and longitudinal position of the sheath may be adjust by the user (e.g., physician) turning, pushing, and/or pulling on a proximal end of the sheath. In those embodiments involving more than one sheath (see, for example FIGS. 12A-12D), the user have further flexibility in making adjustments. In these embodiments, the user may adjust the radial and longitudinal positions of any of the sheaths (and thus the corresponding windows), which collectively will create an overlapping exposure window.

As part of this positioning step, the location of the insulating member or sheath with respect to the lead body may be secured using one of the various stopping members described herein (block 230). Any of the various stopping members described herein may be implemented to help position and secure the radial orientation of the sheath, the longitudinal position of the sheath, or both with respect to the lead body. For example, the user may advance the sheath distally until it makes contact with a longitudinal stop, which thereby confirms alignment of a window (or windows) on the sheath with a corresponding electrode (or electrodes) on the lead body. The user may then rotate the sheath to further direct stimulation energy in a desired fashion.

In some embodiments, an axial adjustment and a radial adjustment of the electrically insulating member 52 over the lead body 50 may be controlled with the use of the first threaded portion 97 and the second threaded portion 99. The first threaded portion and the second threaded portion are described in conjunction with FIGS. 14 and 15. The first threaded portion 97 and the second threaded portion 99 may provide an axial motion of the electrically insulating member 52 over the lead body 50 by rotation of the electrically insulating member 52 over the lead body 50. As the electrically insulating member 52 is rotated, it advances linearly along the length of the lead body 50, exposing the electrode 38 for optimized stimulation. The first threaded portion 97 and the second threaded portion 99 may prevent a lateral movement of the electrically insulating member 52 over the lead body 50. This may ensure the lead body 50 and the electrically insulating member 52 does not rotate chronically to move away from the target tissue (i.e. vagus nerve). The first threaded portion 97 and the second threaded portion 99 may enable a variable portion of an electrode to be exposed (or masked) to optimize stimulation and minimizing stimulation to unwanted tissue.

After positioning and securing the sheath with respect to the lead body, stimulation energy is supplied to the target tissue (block 240). The electrically insulating member 52 may provide masking of electrodes 38 for focusing and directing stimulation energy towards a target tissue and away from other tissues. In an embodiment, the at least one window is an electrically permeable window, and the stimulation may be provided to the at least one electrode through the electrically permeable window. In some embodiments, for example, the implanting physician will monitor both desired and undesired stimulation during the implantation process. Then, depending on the detected results, the physician can further adjust the radial and longitudinal position of the sheaths to further optimize the amounts of desired and undesired stimulation.

In various embodiments, each of the electrodes is disposed around the lead body such that they collectively cover the entire (i.e., 360 degrees) radial surface around the lead body. In another embodiment, the at least one electrode includes a first electrode disposed around the lead body such that it covers a radial surface over 0 to 90 degrees around the lead body defined as a first radial quadrant, a second electrode disposed around the lead body such that it covers a radial surface over 90 to 180 degrees around the lead body defined as a second radial quadrant, a third electrode disposed around the lead body such that it covers a radial surface over 180 to 270 degrees around the lead body defined as a third radial quadrant and a fourth electrode disposed around the lead body such that it covers a radial surface over 270 to 360 degrees around the lead body defined as a fourth radial quadrant. In some embodiments, various electrodes are pointing in different radial directions, while windows are aligned linearly along the sheath, such that at any given position, only one electrode aligns with the window and thereby with a target tissue, and other electrodes are insulated by the electrically insulating member. The electrode that is in alignment with the window may be programmed to provide stimulation to the target tissue.

After the implantation, if the electrode programmed to provide stimulation to the target tissue rotates away from the target tissue, then another electrode from nearby quadrant will be automatically directed toward the target tissue. At that time, the other electrode may be programmed to stimulate the target tissue. Hence there is no need of the implantation operation again to orient the other electrode in the nearby quadrant toward the target tissue.

Thus, the various embodiments of the present invention provide an implantable lead with an axially movable and rotatable electrically insulating member disposed over the lead body having a stopping feature and an adjusting feature to easily place the electrically insulating member over the lead body and orient the electrodes toward a desired target tissue. The implantable lead provides the axial adjustment as well as the radial adjustment abilities of the electrically insulating member over the lead body and further provides locking of the electrically insulating member over the lead body at each axially and rotationally adjusted position. The electrically insulating member may provide masking of electrodes for focusing and directing stimulation energy toward a target tissue and away from other tissues. Hence, the implantable lead may ensure that windows align with the appropriate electrodes. The implantable lead may ensure that the lead body and the insulating member do not rotate chronically to move away from the target tissue.

Example 21 concerns an implantable medical lead for stimulating or sensing a target tissue, the implantable medical lead comprising: a lead body including a proximal end portion, a distal end portion, and at least one electrode extending circumferentially around at least a portion of the lead body, the lead body having a longitudinal axis; and at least one spacing member disposed around and rotationally coupled to a portion of the lead body, the at least one spacing member having a centerline defined along a longitudinal axis of the spacing member, wherein the centerline is offset from the lead body longitudinal axis by an offset distance; wherein the at least one spacing member is configured to adjust a spacing between the at least one electrode and the target tissue upon rotation of the lead body.

In example 22, the lead of example 21, wherein the non-circular cross-sectional spacing member has a spiral-shaped cross-sectional geometry.

In example 23, the lead of any of examples 21 or 22, wherein the at least one spacing member has a non-circular cross-sectional geometry.

In example, 24, the lead of example 23, wherein the non-circular cross-sectional spacing member has an oval-shaped cross-sectional geometry.

In example 25, the lead of any of examples 21-24, wherein the spacing between the target tissue and the electrode is adjustable from between about 1 mm and about 7 mm, depending upon the rotational position of the spacing member with respect to the target tissue.

In example 26, the lead of any of examples 21-25, wherein the spacing member is disposed over the at least one electrode and includes at least one exposure window configured to expose the at least one electrode to the target tissue.

In example 27, the lead of example 26, wherein the at least one window is selected from the group consisting of a physical window and an electrically permeable window.

In example 28, the lead of any of examples 21-27, wherein the spacing member has a length of between about 2 mm and about 5 mm.

In example 29, the lead of any of example 21-28, wherein the spacing member is tapered along its length such that a distance between the centerline of the spacing member and an outer surface of the spacing members varies along its length.

In example 30, the lead of any of examples 21-29, wherein the at least one spacing member includes a plurality of spacing members disposed at spaced-apart locations along the lead body and further wherein the at least one electrode is disposed between two of the plurality of spacing members.

In example 31, the lead of example 30, wherein the plurality of spacing members are of different geometric shapes.

In example 32, the lead of either of examples 30 or 31, wherein each of the plurality of spacing members has a different major diameter, such that the implantable medical lead has a generally tapered profile.

In example 33, an implantable medical lead for stimulating or sensing a target tissue, the implantable medical lead comprising: a lead body including a proximal end portion, a distal end portion, and at least one electrode extending circumferentially around at least a portion of the lead body, the lead body having a first longitudinal axis; and a plurality of spacing members disposed around and rotationally coupled to a portion of the lead body, the spacing members having a non-circular cross-section and a centerline defined along a longitudinal axis of the spacing members, wherein the centerline is offset from the lead body longitudinal axis by an offset distance; wherein the spacing members are configured to adjust a spacing between the at least one electrode and the target tissue upon rotation of the lead body.

In example 34, a method of providing electrical stimulation to a target tissue site, while minimizing stimulation to an extraneous tissue site, the method comprising: implanting an implantable lead within a patient's body, the implantable lead including: a lead body having a proximal end portion, a distal end portion, and at least one electrode extending circumferentially around at least a portion of the lead body, the lead body having a longitudinal axis; and at least one spacing member disposed around and rotationally coupled to the distal end portion of the lead body, the at least one spacing member having a centerline defined along a longitudinal axis of the spacing member, wherein the centerline is offset from the lead body longitudinal axis by an offset distance; and rotating the lead body to adjust a spacing between the at least one electrode and the target tissue site.

In example 35, the method of example 34, further comprising stimulating a body tissue with the at least one electrode.

In example 36, the method of example 35, further comprising sensing an electrical stimulation at the target tissue site and further rotating the lead body, based on a target tissue site sensed stimulation level.

In example 37, the method of example 36, wherein the target tissue site is a vagus nerve such that the rotating step comprises adjusting a spacing between the vagus nerve and the at least one electrode.

In example 38, the method of any of examples 34-37, wherein the spacing member has a non-circular cross-sectional geometry selected from the group consisting of: an oval geometry and a spiral geometry.

Figure 17A:
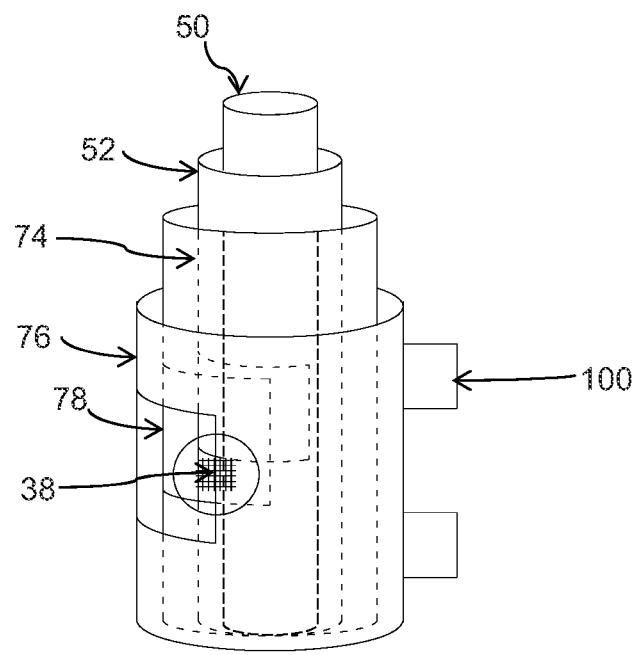
FIGS. 17A and 17B show perspective views of an implantable lead including rotational sheaths having protrusion features, according to various embodiments.
Figure 17B:
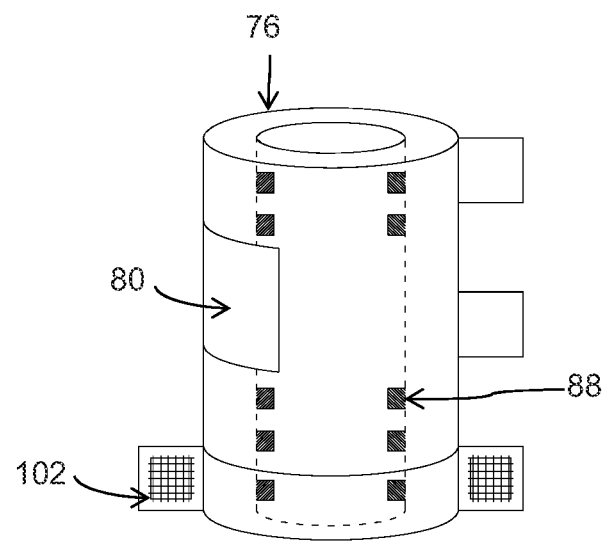

FIGS. 17A and 17B show various embodiments of insulating members including features disposed over a distal portion of a lead and configured to direct stimulation energy toward the target tissue (e.g., the vagus nerve) and away from other surrounding tissues (e.g., adjacent muscles). The insulating members of FIGS. 17A and 17B may be used with any of the various implantable leads 14 described above. According to various embodiments, FIGS. 17A and 17B are used, for example, with the configuration shown and described above with reference to FIGS. 12B-12D. In these embodiments, the multiple insulating members 52, 74, 76 can be rotated with respect to one another to adjust the size of an exposure window for exposing the electrode 38. As described above, the insulating members may include cooperating threads 82, 86, 88 as shown, for example, in FIGS. 12B-12D. The male threads 82 of the electrically insulating member 52 are configured to be engaged with the female threads 86 of the electrically insulating member 74 to fix (or hold) the electrically insulating members (such as 52, 74 and 76) together. According to various embodiments, the exposure window may be a physical opening or an electrically permeable portion.

As shown in FIGS. 17A and 17B, the outermost insulating member or sheath 76 includes one or more protruding portions 100 disposed at a defined location along the length of the insulating member. The protruding portion (or portions) 100 may be disposed at a location corresponding to or adjacent to one or more of the electrodes 38 along the lead body 50, such that the user (e.g., a physician) can adjust the position of the protruding portion 100 to adjust a distance between the at least one electrode 38 and a first surrounding tissue adjacent to the defined portion. By this technique, the user may urge the electrode 38 closer to a desired target stimulation site (e.g., the vagus nerve) and/or further from undesired adjacent tissues. For example, according to various embodiments, the physician rotates or adjusts the location of the protruding portion 100 such that it is disposed adjacent to the undesired adjacent tissues, thus affecting a spacing or separation between the undesired tissues and the stimulation electrode 38.

In accordance with various embodiments, the protruding portion 100 can extend over the defined portion of the insulating member in a continuous manner. In other embodiments, the protruding portion 100 can extend over the defined portion of the insulating member in a discrete manner. In yet other embodiments, the protruding portion 100 can extend over the defined portion continuously. For example, the defined portion of the lead 14 may include several protruding portions 100 disposed at discrete locations over the defined portion. In accordance with the continuous pattern of the protruding portion 100, the defined portion is the length from a first lateral end of the protruding portion 100 to a second lateral end of the protruding portion 100. In accordance with the discrete pattern including multiple protruding portions 100, the defined portion includes a length of the lead 14 or the outer surface of the insulating member 76 from a lateral end (close to a first lateral end of the lead 14) of the first protruding portion 100 to a lateral end (close to a second lateral end of the lead 14) of the last protruding portion 100. In some embodiments, the defined portion extends across a portion of the length of the insulating member 76 or the lead 14. In some other embodiments, the defined portion extends along an entire length of the insulating member 76. In accordance with various embodiments, the protruding portion 100 is disposed or formed to project linearly in the same direction.

In some embodiments, the protruding portion 100 is integrally formed with the electrically insulating member 76. In other embodiment, the protruding portion 100 is structurally distinct and separately attached to the electrically insulating member 76 during placement of the lead 14 inside a patient's body. In various embodiments, the protruding portion 100 is an insulating portion and is configured to insulate body tissues from a stimulation caused by the at least one electrode 38. According to various exemplary embodiments, the protruding portion may extend radially a distance of from about 1 mm to about 5 mm from the outer surface of the insulating member. As described above and illustrated in FIGS. 17A-17B, the protruding portion 100 is provided only on the outermost insulation member 76. In other embodiments, however, the protruding portions 100 may be located on the inner insulating members (e.g., 52 and/or 74) or on both the outer and inner members. In some embodiments of the present invention, as shown in FIG. 17B, the outermost insulating member 76 is provided with an external tie down feature 102. The tie down feature 102 is configured to lock surrounding tissues with respect to the window 78 of the insulating member 76 at an optimal position.

Figure 18A:
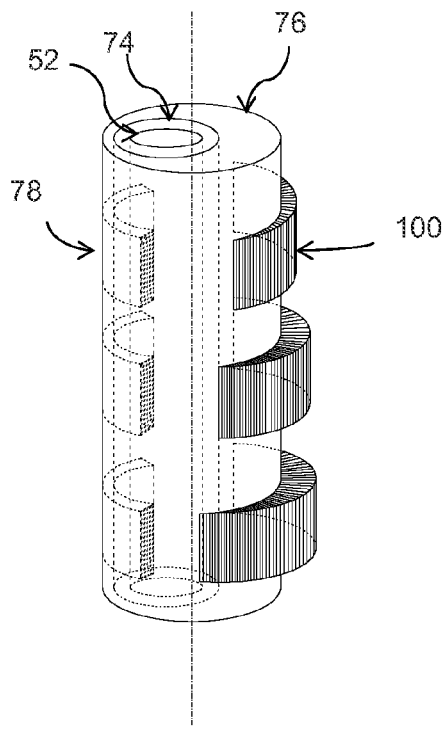
FIGS. 18A-18D show perspective views of an implantable lead having protrusion features, according to various embodiments.
Figure 18B:
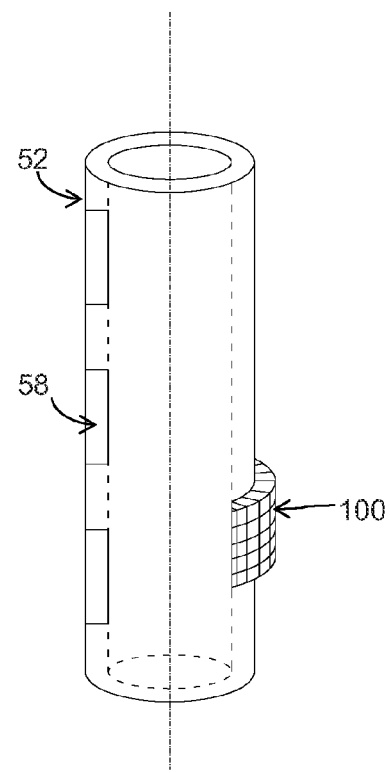
Figure 18C:
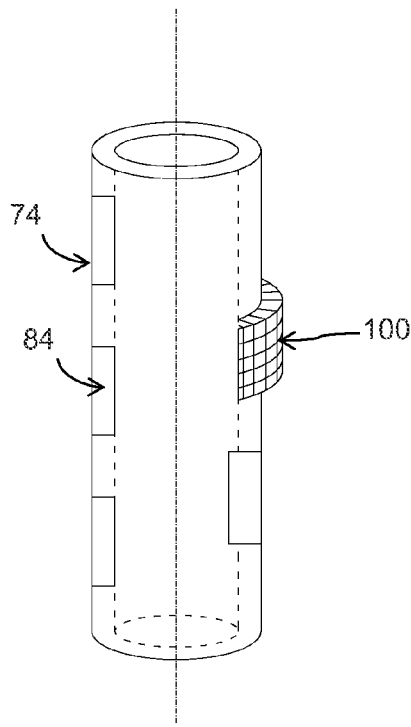
Figure 18D:
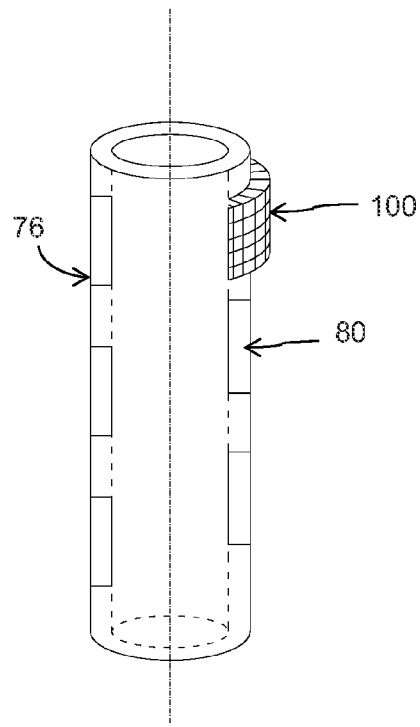

FIGS. 18A-18D show various embodiments of insulating sheaths including one or more protruding portions 100 located on a distal portion of a lead. FIG. 18A shows three insulating sheaths 52, 74, 76 disposed inside one another. FIGS. 18B-18D shows each of the insulating members 52, 74, 76 individually. As shown in FIGS. 18B-18D, each of the insulating members 52, 74, 76 includes a protruding portion 100. In some embodiments, for example, the implantable lead 14 is arranged in a manner, wherein the electrically insulating members (such as 52, 74 and 76) include an inner insulating member 74 and an outer 76 insulating member. The inner insulating member 74 is provided with the protruding portion 100 and the outer insulating member 76 is provided with a window or compartment such that the protruding portion 100 is configured to extend from the inner insulating member 74 through the compartment of the outer insulating member 76 and beyond the outer surface of the insulating member 76. The inner insulating member 74 and the outer insulating member 76 are configured to be relatively rotated to a defined degree that is dependent on a dimension of the spaced compartment. The dimension of the spaced compartment is further configured to limit an exposure of the at least one electrode 38 through the at least one window 78. According to various exemplary embodiments, the window or compartment is dimensioned to allow the protruding portion 100 to rotate through an angle of between about 10 and about 150 degrees.

In some other embodiments, for example, the implantable lead 14 is arranged in a manner, wherein the inner insulating member is a first inner insulating member 74, the implantable lead 14 further comprising a second inner insulating member 52 such that the second inner insulating member 52 includes a protruding portion 100 and the first inner insulating member 74 includes a window or compartment such that the protruding portion 100 is configured to extend from the second inner insulating member 52 through the spaced compartment of the first inner insulating member 74 and a second spaced compartment of the outer insulating member 76, the second spaced compartment different than the spaced compartment of the outer insulating member 76. FIG. 18A, for example, shows an embodiment where each of the protruding portions 100 extends radially outward through a corresponding window in the overlying sheath. Thus, as shown, in the fully assembled configuration with each of the insulating members 52, 74, 76 disposed inside one another, each of the protruding portions 100 extends outside of the outer insulating sheath 76.

Figure 19A:
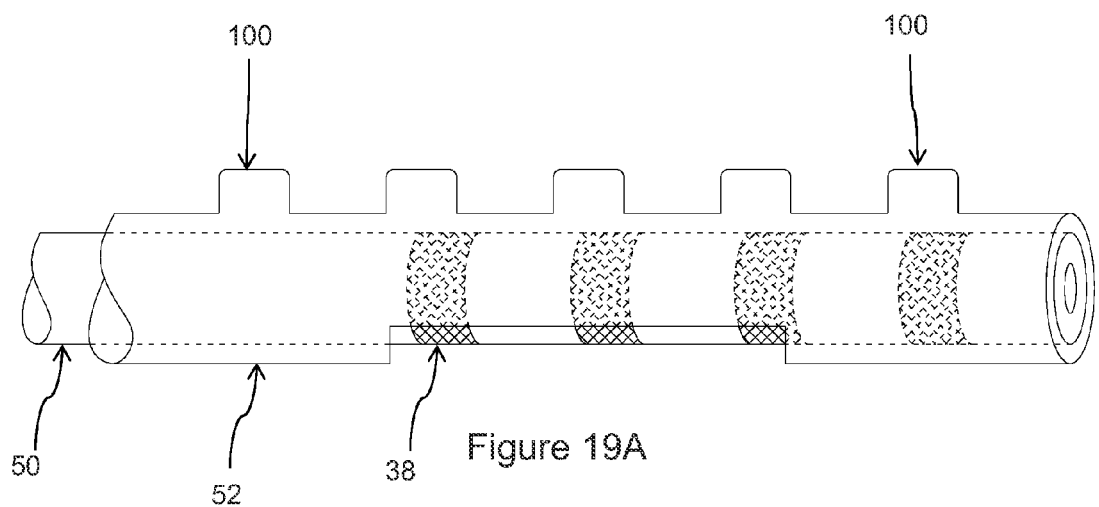
FIGS. 19A and 19B show perspective views of an implantable lead having protrusion features, according to various embodiments.
Figure 19B:
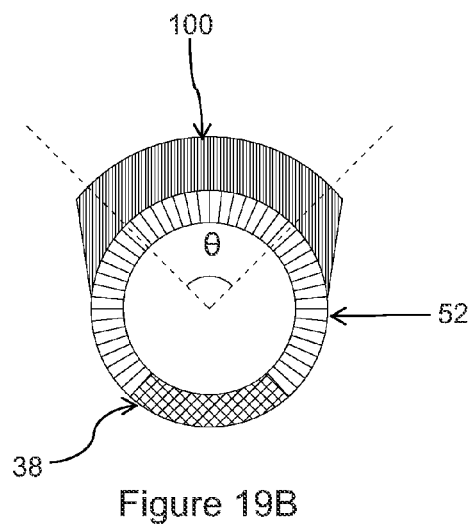

FIGS. 19A-19B illustrates perspective and cross-sectional views of embodiments of a distal portion of a lead 14 including an insulating member 52 having one or more protrusions 100. In some embodiments, as shown, the protruding portion 100 has a non-circular or asymmetric cross-section. As shown in FIG. 19A, the insulating sheath 52 has multiple discrete protrusions 100, and each of the protrusions 100 is generally aligned with an electrode 38 located on the lead body 50. Such a configuration allows each of the protrusions 100 to urge a corresponding electrode 38 toward a target site. According to other embodiments, the sheath may have more or fewer protrusions than corresponding electrodes 38 on the lead body 50. As shown in FIG. 19B, the protrusion 100 may be disposed on a portion of the insulating sheath generally opposite the location of an exposure window adapted to electrically expose the electrode portion 38. In this way, the protrusion 100 may operate to urge the exposure window (and thus the electrode 38) toward target tissues and away from surrounding tissues. According to various embodiments, the protrusion 100 may extend circumferentially around a portion of the insulating sheath such that it extends through an angle (shown as angle "θ" in FIG. 19B) of between about 10 and about 180 degrees. According to exemplary embodiments, the protrusion 100 extends through an angle of between about 25 and about 120 degrees.

Figure 20:
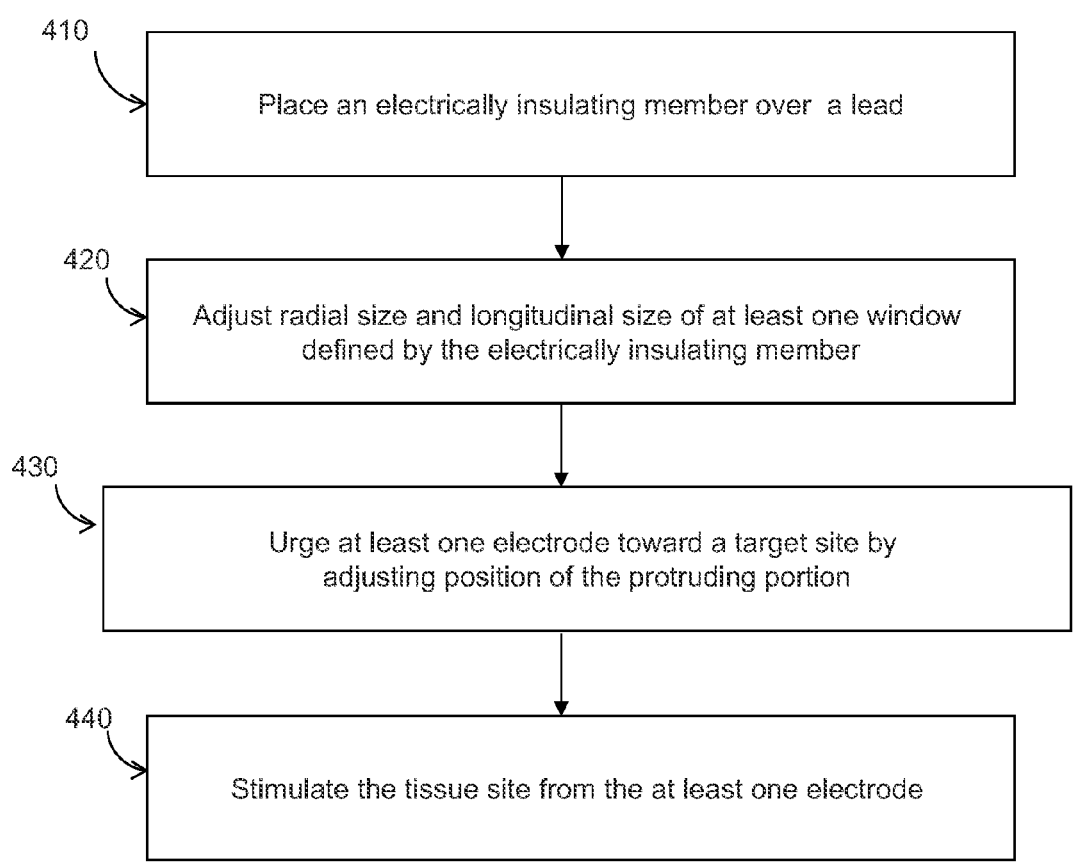
FIG. 20 is a flowchart illustrating a method of directing electrical stimulation at a tissue site, according to various embodiments.

FIG. 20 is a flow chart illustrating a method 400 for providing electrical stimulation at a tissue site. As shown, the method 400 includes placing an electrically insulating member over a lead having at least one electrode, the insulating member defining the at least one window configured to expose at least a portion of the electrode (block 410). As described above, the insulating member further includes a protruding portion disposed linearly on a defined portion of the insulating member. The method, according to various embodiments, further includes adjusting the amount of exposure of the electrode to the target tissue by adjusting at least one of the radial size and the longitudinal size of the at least one window. In various embodiments, the insulating member is adjusted so that the at least one window faces toward the target tissue site (e.g., the vagus nerve) desired for stimulation (block 420). A user (e.g., a physician) may then advance the lead and insulating member (either together or separately) to a location near the target site. Once the window is placed in proximity of the target tissue site and the amount of electrode exposure is adjusted, the position of the protruding portion is adjusted by rotating the at least one insulating member (block 430). The position of the protruding portion is adjusted in such a manner that the distance between the at least one electrode and the first surrounding tissue such as extraneous structures is greater than a distance between the at least one electrode and the target tissue. After adjusting the position of the protruding portion, the target tissue site is stimulated from the at least one electrode (block 440). According to various embodiments, the lead body may then be rotated to optimize alignment of the electrode structure (i.e., electrodes which extend across only a circumferentially limited segment of the lead body) with the window. According to various embodiments, the method further includes sensing electrical activity at one or both of a desired target tissue site and a surrounding (i.e., extraneous) tissue site, upon delivery of stimulation through the electrode. Based on the sensed stimulation at one or both of the target tissue site and the extraneous tissue site, the physician may then further adjust the spacing of the electrode with respect to these sites by further rotation of the lead body (and the spacing members). This process may be repeated one or several times, until a desired amount of electrical stimulation is sensed at one or both of the target tissue site and the surrounding tissue site.

Figure 21A:
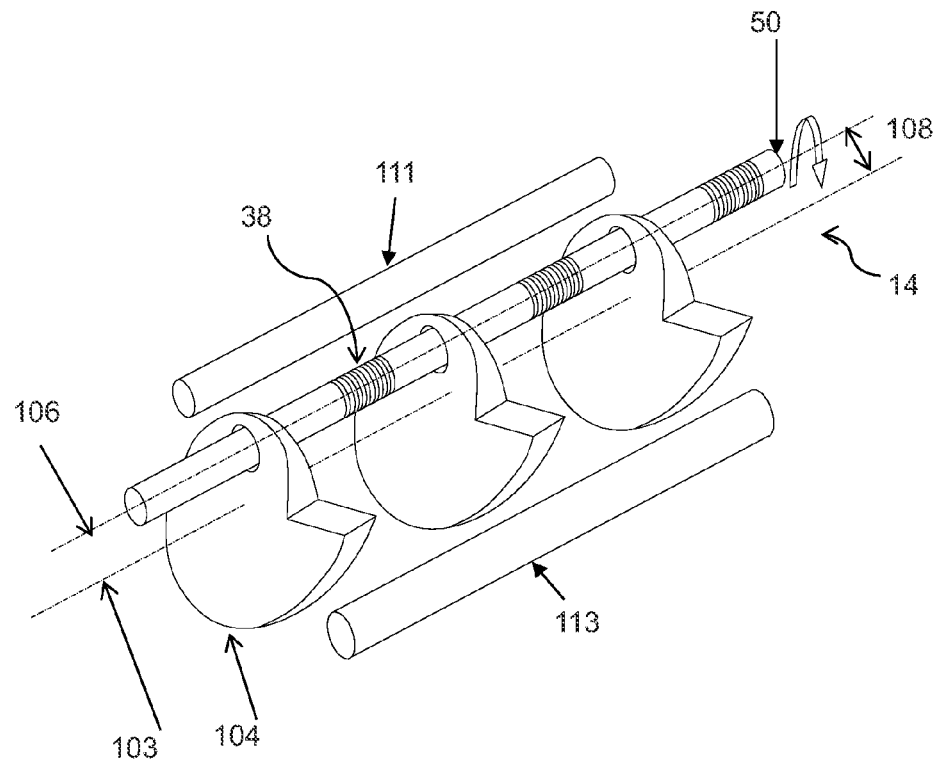
FIGS. 21A-21C are perspective views of an implantable lead for tissue stimulation, according to various embodiments.

FIG. 21A is a perspective view of an implantable lead 14 for use in an implantable system such as a CRM system 10 or an implantable neurostimulation system 110, according to various embodiments. As shown, the lead 14 includes a lead body 50 (having a longitudinal axis or centerline 106) and one or more spacing members 104 (having a longitudinal axis or centerline 103) coupled at various locations along the length of the lead body. In various embodiments, the spacing members 104 may be rotationally coupled to the lead body, such that rotational motion of the lead body results in a corresponding rotational motion of the members. As shown in FIG. 21A, the members 104 are configured such that the transverse section has a gradually increasing radius about the circumference. According to other embodiments, the members 104 are circular in cross-section. In other embodiments, the member 104 may have a cross-sectional configuration having a gradually increasing radius about the circumference (see, e.g., FIGS. 21A and 21B), an oval configuration (see, e.g., FIG. 22), or a tapered geometry (see, e.g., FIGS. 23A, 23B and 19C).

The lead body 50 includes one or more electrodes 38 disposed at various locations along the length of the lead body. These electrodes 38 are coupled to a pulse generator of the CRM system 10 or the neurostimulation system 110 and allow the systems to stimulate or sense target tissue. As further shown, the longitudinal axis 106 of the lead body 50 is offset a distance 108 from the centerline 103 of the members 104. This offset distance 108 between a longitudinal centerline of the members 104 and the lead body 50, allows the user (e.g., a physician) to adjust the position of the electrodes 38 on the lead body 50 with respect to a target tissue site 111 (e.g., the vagus nerve) by rotating the lead body 50. In particular the members 104 may operate to urge the electrodes 38 of the lead body 50 toward a target tissue site 11 or away from an undesired site 113 (e.g., muscles). By adjusting the radial position of the lead body (and thus the radial position of the members 104), a user can influence the spacing between the electrodes and a tissue site. According to various embodiments, the lead body has a diameter of from about 1 mm to about 4 mm (e.g., about 2.5 mm) and the distance 108 is between about 1 mm and about 4 mm. In one exemplary embodiment, the lead body has a diameter of about 2 mm, the offset is about 2 mm, and the major diameter of the member 104 is about 8 mm. This embodiment enables the user to adjust spacing from a tissue site by between about 1 mm and about 7 mm.

Figure 21B:
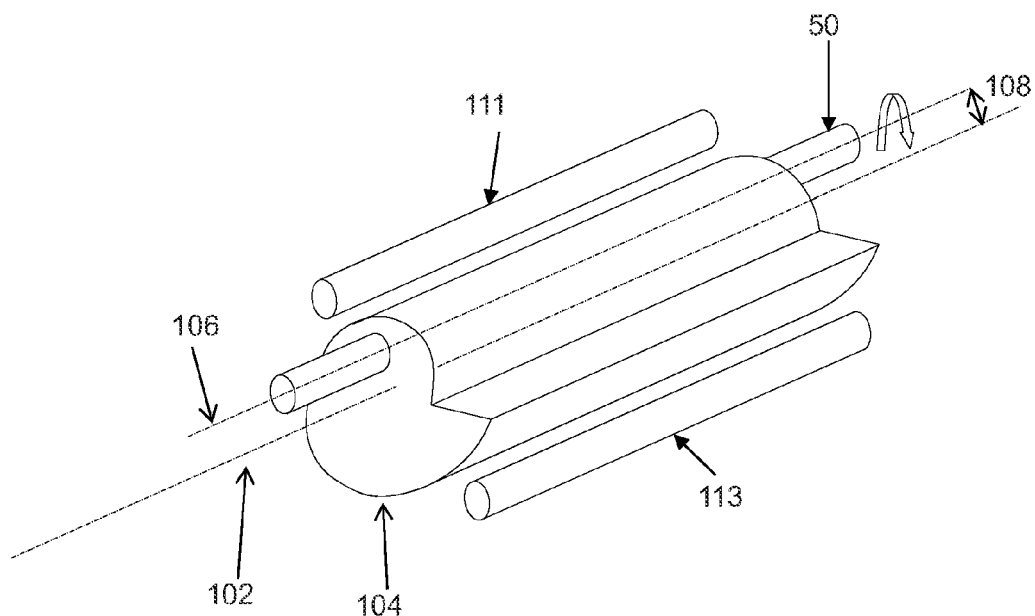

As shown in FIG. 21A, the members 104 include three discrete members each separately coupled to the lead body 50. In various embodiments, the members 104 may be placed at locations corresponding to one or more of the electrodes 38. In other embodiments, the members 104 may be placed at other locations helpful in controlling spacing with respect to a tissue site. In some embodiments, the geometric shapes of each of the members 104 are the same (or substantially the same), while in other embodiments one or more of the members 104 have different shapes. Further, in embodiments having multiple discrete members 104, a spacing distance between the members may be the same or may vary. In other embodiments, as shown in FIG. 21B, the member 104 is a unitary or continuous structure extending along a desired portion of the lead body. The continuous segment can include an optional window or electrically permeable surface to expose the electrode 38. Alternatively, the continuous segment can be located or positioned adjacent one or more electrodes 38. According to various embodiments, the continuous member 104 has a length (i.e., a dimension oriented along the longitudinal axis of the lead body) of between about 1 mm and about 10 mm. According to some embodiments, the member 104 has a length of from about 2 mm to about 5 mm.

Figure 21C:
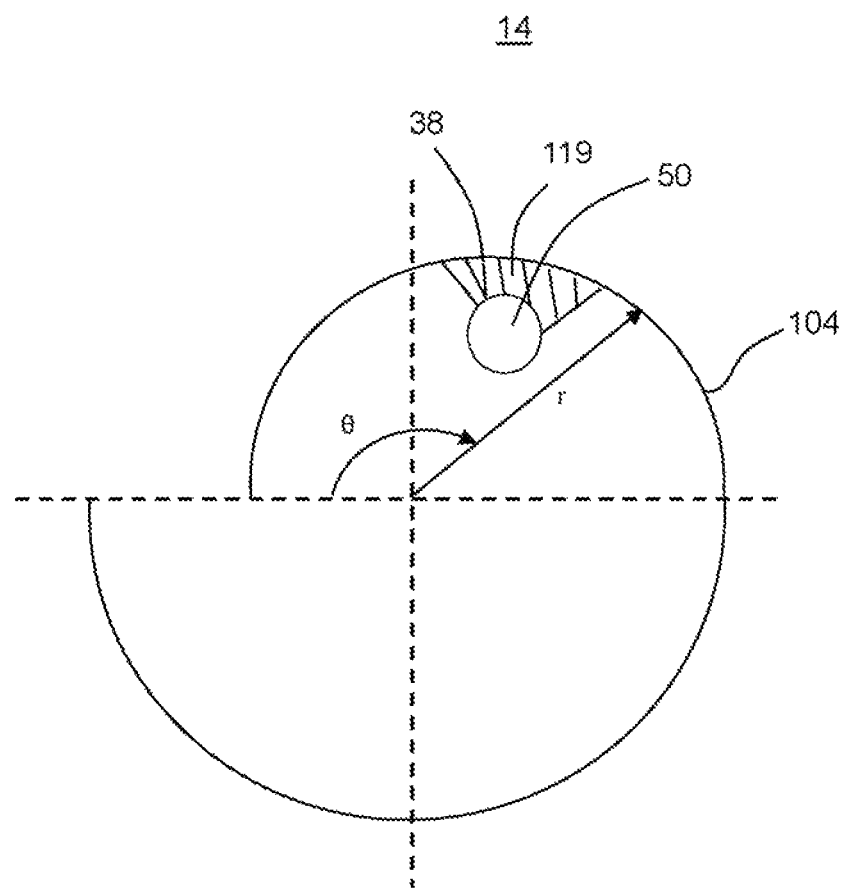

FIG. 21C is a cross-sectional view of an implantable lead 14 through a member 104 according to various exemplary embodiments. As shown, the member 104 has a radius (r), extending from a central point to its perimeter, that increases continuously as the angle theta increases. According to various embodiments, the member 104 may have an equiangular or logarithmic spiral-shaped cross-section (e.g., a nautilus shell). As shown in FIG. 21C, the member 104 of the lead 14 includes an electrode exposure window 119 disposed between the electrode 38 and an outer periphery of the lead 14. In various embodiments, this window 119 may be either an open area or an electrically conductive or permeable area. The window 119 can be configured to allow electrical communication between a portion of the electrode 38 and adjacent body tissues. Various embodiments for such exposure windows are disclosed in U.S. provisional patent application 61/578,628, filed on Dec. 21, 2011, which is hereby incorporated by reference.

In some embodiments, the target tissue site 111 is a vagus nerve such that the member 104 is configured to adjust a distance between the vagus nerve and the at least one electrode 38. The distance can be adjusted upon rotation of the lead body 50, which is capable of rotating from 0 degrees to 360 degrees. As the device is rotated, the electrode 38 may be urged closer to the vagus nerve 111 and away from adjacent muscles 113, so as to help decrease capture threshold for the vagus nerve and increase stimulation threshold for the adjacent muscles.

Figure 22:
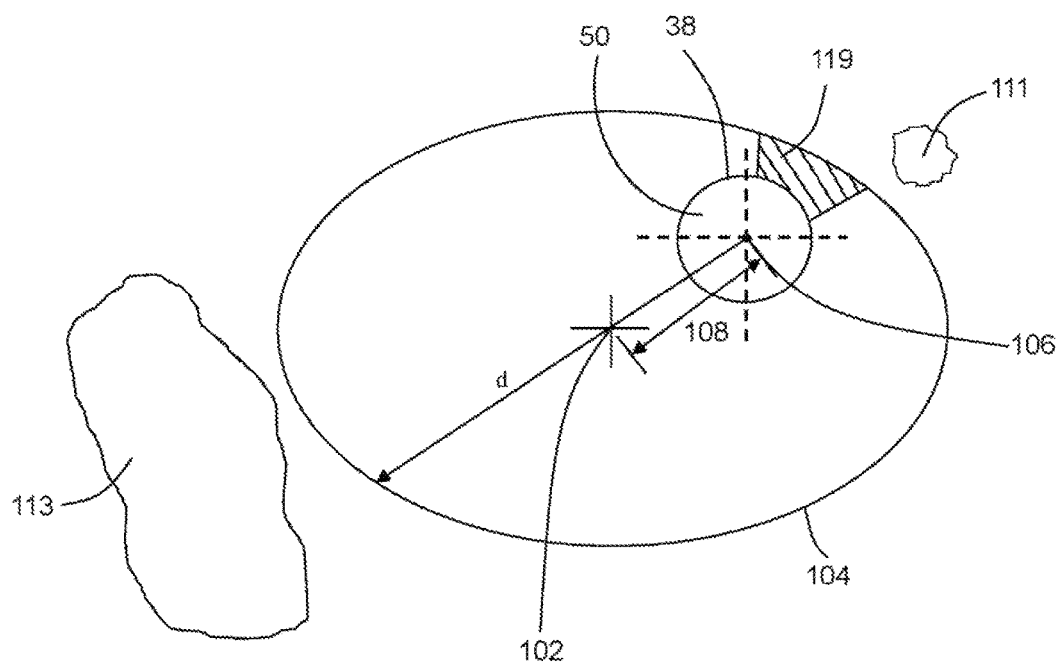
FIG. 22 is a sectional view of a portion of an implantable lead in accordance with an embodiment of the present invention.

FIG. 22 shows the cross-section of exemplary embodiments of an implantable lead 14 having a non-circular cross-sectional member 104. In particular, as shown, the member 104 has a generally oval-shaped cross-section. In such embodiments, as shown, a longitudinal axis 106 of the lead body 50 is spaced by a distance (d) from an outer peripheral surface of the lead 14. As further shown in FIG. 22, the lead body 50 includes an electrode 38 (e.g., a ring electrode) which generally extends around a portion or the entire circumference of the lead body 50. Also shown is an electrode exposure window 119 disposed between the electrode 38 and an outer periphery of the lead 14. In various embodiments, this window 119 may be either an open area or an electrically conductive or permeable area. The window 119 can be configured to allow electrical communication between a portion of the electrode 38 and adjacent body tissues. Various embodiments for such exposure windows are disclosed in U.S. provisional patent application 61/578,628, filed on Dec. 21, 2011, which is hereby incorporated by reference.

Depending on the rotational orientation of the lead 14, the distance (d) from the longitudinal axis 106 to the target site (e.g., the vagus nerve) varies. Thus, in a similar manner, the distance between the electrode 38 and the target site varies. This configuration allows a user (e.g., a physician) to vary a distance between the exposed portion of the electrode 38 and surrounding body tissue, by rotating the lead 14. According to alternative embodiments, the lead 14 does not include a structurally independent or distinct member 104, but instead the lead body 50 has an overall oval-shaped cross-section.

Figure 23A:
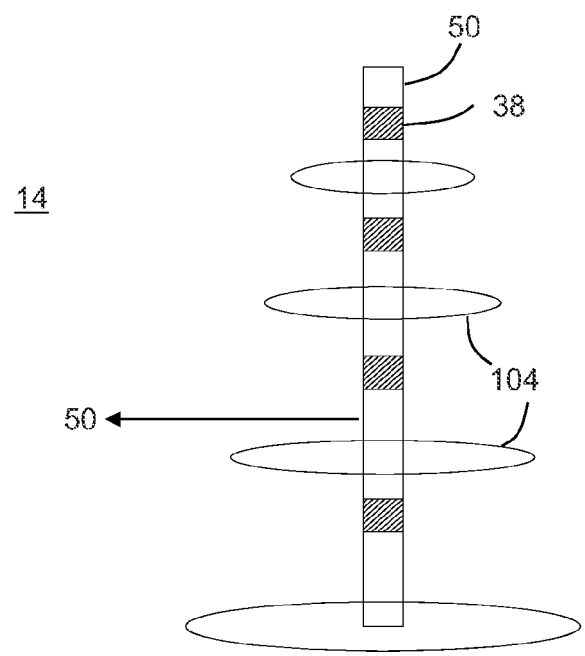
FIGS. 23A-23B are schematic views of implantable leads having a diameter that varies along a length of the lead, according to various embodiments.
Figure 23B:
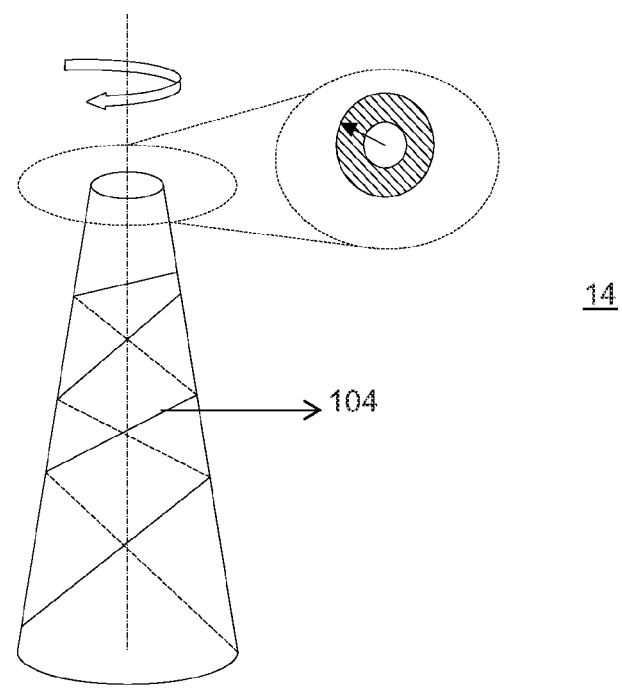

FIGS. 23A-23B show schematic views of exemplary embodiments of an implantable lead 14 for use in an implantable system such as the CRM system 10 or the neurostimulation system 110, according to various embodiments. As shown in FIG. 23A, the lead 14 includes a lead body 50 and multiple members 104 spaced at various locations along the length of the lead body. As shown, the lead body 50 includes multiple (e.g., four) electrodes 38 spaced along its length. The members 104 are rotationally coupled to the lead body 50, such that rotation of the lead body results in a corresponding rotation of the members 104. Also, the members 104 are coupled to the lead body at locations between the electrodes 38, such that the electrodes remain exposed to adjacent body tissues. As further shown, the diameter of the members 104 increases moving from top to bottom in FIG. 23A. These increasing diameters allow for different amounts of spacing between the various electrodes and surrounding body tissues. The dimensions of each of the members 104 may be selected to optimize spacing for a given anatomical region of the body. According to various exemplary embodiments, the smallest of the members 104 has a diameter of between about 2 and about 5 mm. Each succeeding member 104 then increases in diameter by between about 20 and about 70 percent over the previous member 104. In some embodiments, the diameters of the members 104 may be selected to create an effectively tapered shape along the length of the lead 14. Other size configurations are also possible.

In other embodiments, the tapered shape can be formed in a continuous manner as illustrated in FIG. 23B. The tapered shape/geometry can be designed in a converging or diverging manner to accommodate stimulation for non-uniform anatomy of the target tissue/site 111. FIGS. 23A and 23B illustrate examples of tapered non-circular cross-sectional geometries that are either converging or diverging in shape from one location to another location at the lead body 50.

Figure 24A:
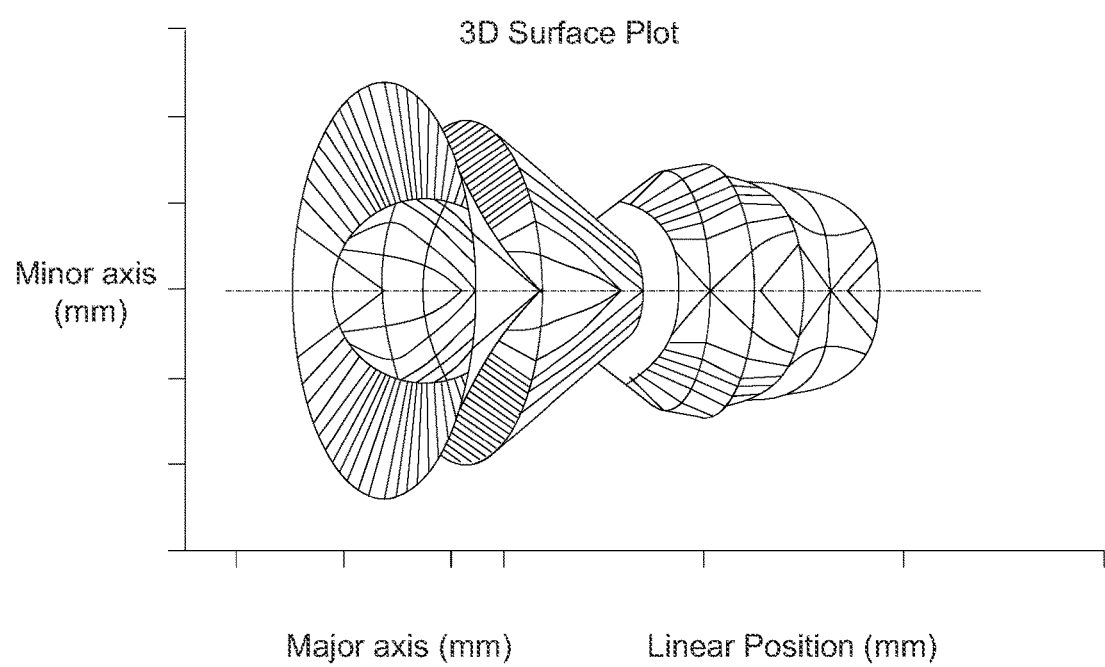
FIGS. 24-24C show exemplary diameter profiles along the length of an implantable lead, according to various embodiments.
Figure 24B:
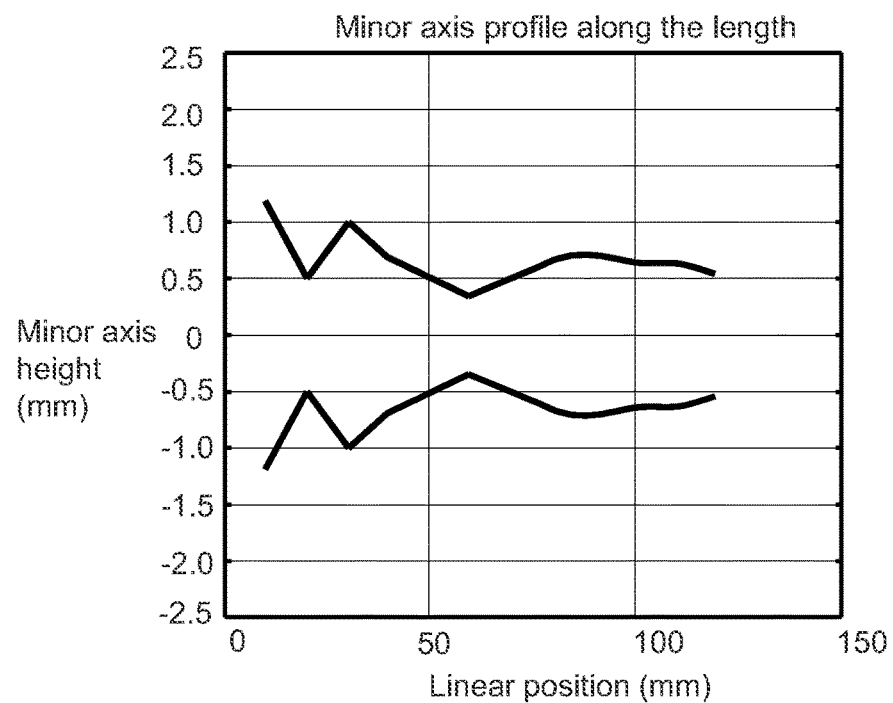
Figure 24C:
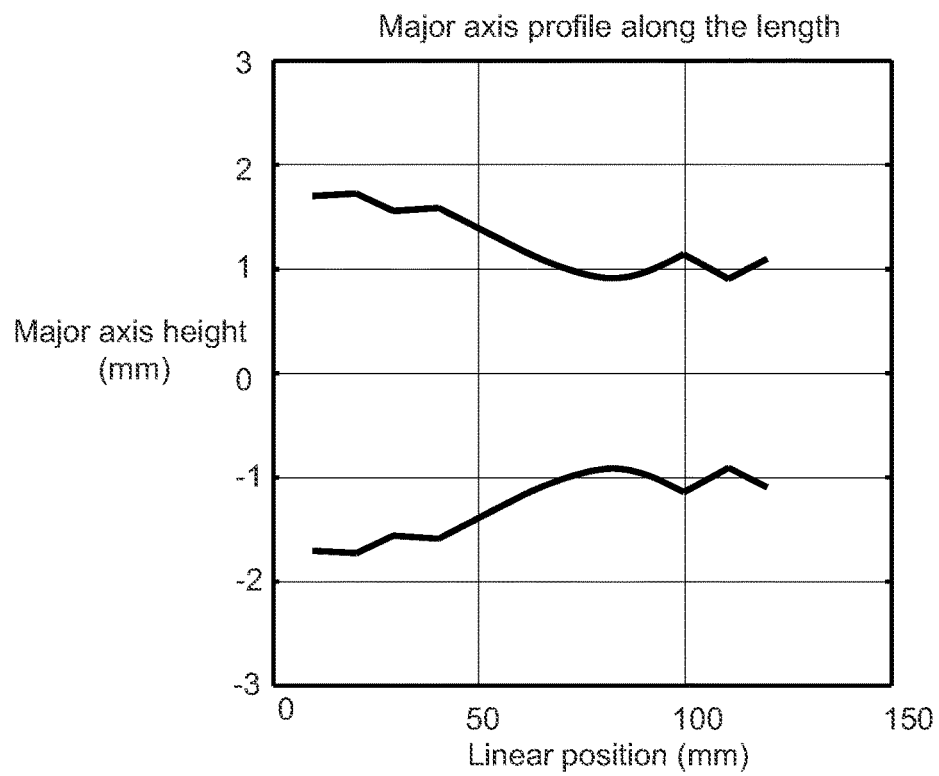

FIGS. 24A-24C show other exemplary profiles of an implantable lead 14. As shown, in these embodiments, the overall lead diameter is increasing and decreasing at various locations along a length of the lead corresponding to a desired stimulation (or sensing) tissue site. Again, the precise dimensions will vary depending upon the particular anatomical location being stimulated. FIG. 24A shows a 3D surface plot of the non-circular cross-sectional segment that converges from a first end of the lead body 50 for a certain distance along its length, then diverges toward other end of the lead body 50 with a tapered width. In such embodiments, the converging and the diverging portions of the members 104 may be symmetric or asymmetric in shape. In other embodiments, the members 104 may include several such converging and diverging portions alternatively or randomly repeated one after another to create an entirely different kind of shape. In other embodiments, the tapered shape of the members 104 may be defined based on custom requirements and shape of the target tissue or stimulation requirements at variable distances along the target tissue 111. FIGS. 24B and 24C show other exemplary profiles drawn on a Cartesian coordinate system. The major axis represents height of the non-circular cross-sectional segment at a particular point, while the minor axis represents linear length of the non-circular cross-sectional segment at a particular point. In each of the embodiments shown in FIGS. 24A-24C, the lead 14 includes one or more electrodes located at a fixed distance from a longitudinal centerline of the lead 14. In this way, a distance between the electrodes and the target tissue 111 (or other extraneous tissue 113) may be varied by rotation of the lead body. In these embodiments, however, the distance between any given electrode and the surrounding body tissue will vary based on the profile of the members 104 along the length of the lead 14.

Figure 25:
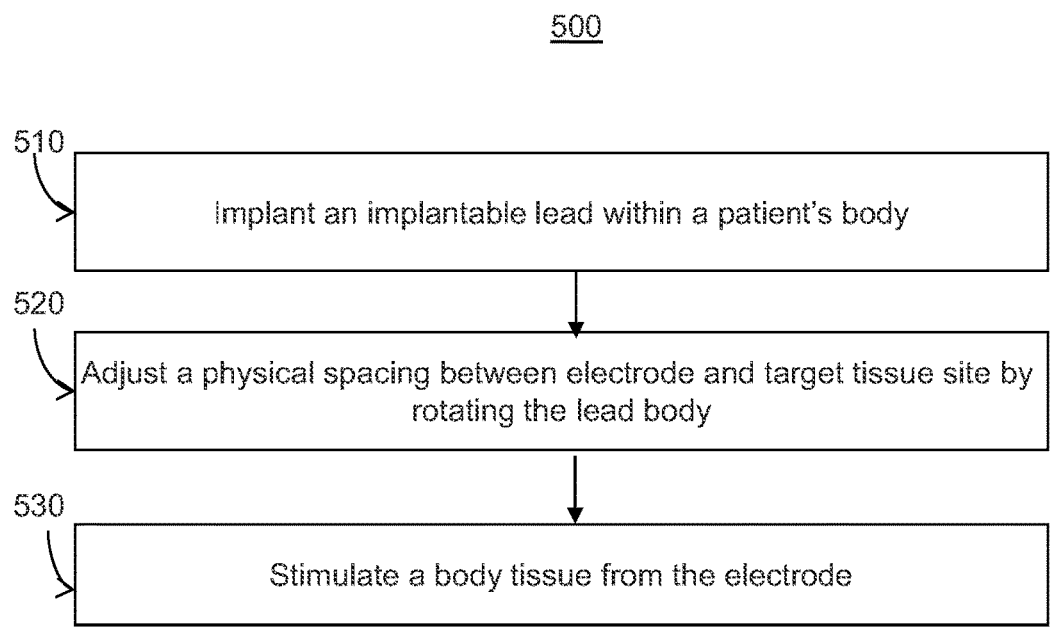
FIG. 25 is a flowchart illustrating a method of providing electric stimulation to a target tissue site while minimizing/controlling stimulation to surrounding tissue.

FIG. 25 is a flow chart illustrating a method 500 of providing electrical stimulation to a target tissue site, while minimizing/reducing stimulation to an extraneous tissue site, using any of the various described embodiments. The method 500 includes implanting an implantable lead 14 within a patient's body (block 510). In some embodiments, the target tissue site is the vagus nerve and the extraneous tissue site is a muscle near the vagus nerve. In various other embodiments, the target tissue site and the extraneous tissue site may be other nerves or tissues or muscles or body locations. The method 500 further includes adjusting a physical spacing between at least one electrode on the lead and the target tissue site by rotating the lead body, which in turn causes a rotation of the spacing members that are rotationally coupled to the lead body (block 520). The rotational adjustment of the lead body, which causes a corresponding rotation of the spacing members, effects a change in the distance between the target tissue site and the at least one electrode, due to the offset between a first centerline of the lead body and a second centerline of the spacing members. Based on requirements and the anatomy of the target tissue site, the rotational adjustment in association with the various shapes of the members can position the electrodes at an appropriate distance from the target tissue site, while simultaneously adjusting distance between the extraneous tissues from the electrodes. The method further includes stimulating the target tissue site (or a body tissue near the target tissue site) from the at least one electrode (block 530). According to various embodiments, the method further includes sensing electrical activity at one or both of a desired target tissue site and an extraneous tissue site, upon delivery of stimulation through the electrode. Based on the sensed stimulation at one or both of the target tissue site and the extraneous tissue site, the physician may then further adjust the spacing of the electrode with respect to these sites by further rotation of the lead body (and the spacing members). This process may be repeated one or several times, until a desired amount of electrical stimulation is sensed at one or both of the target tissue site and the extraneous tissue site.

In example 39, an implantable medical lead includes a lead body including a proximal end portion, a distal end portion and at least one electrode extending circumferentially around at least a portion of the lead body and a sheath member that extends axially over a portion of the lead body between the proximal end portion and the distal end portion, the sheath formed of an electrically insulating member defining at least one window. In this example, the electrically insulating member is configured to rotate around the lead body such that in a first radial position a first portion of the at least one electrode is exposed through the at least one window and a second portion of the at least one electrode is covered by the electrically insulating member and each of the lead body and the electrically insulating member has corresponding features configured to secure the electrically insulating member in a desired orientation on the lead body.

Example 40 is the implantable lead of example 39, wherein the at least one window is an electrically conductive section of the electrically insulating member.

Example 41 is the implantable lead of either of examples 39 or 40, wherein the at least one electrode extends 360 degrees around the lead body.

Example 42 is the implantable lead of any of examples 39-41, wherein the at least one electrode includes a first electrode disposed around the lead body such that it covers a first radial quadrant of the lead body corresponding to a radial surface extending from about 0 to 90 degrees around the lead body; a second electrode disposed around the lead body such that it covers a second radial quadrant of the lead body corresponding to a radial surface extending from about 90 to 180 degrees around the lead body; a third electrode disposed around the lead body such that it covers a third radial quadrant of the lead body corresponding to a radial surface extending from about 180 to 270 degrees around the lead body; and a fourth electrode disposed around the lead body such that it covers a fourth radial quadrant of the lead body corresponding to a radial surface extending from about 270 to 360 degrees around the lead body.

Example 43 is the implantable lead of any of examples 39-42, wherein the at least one electrode includes a first electrode disposed around the lead body such that it covers a first radial quadrant of the lead body corresponding to a radial surface extending from about 0 to 90 degrees around the lead body; a second electrode disposed around the lead body such that it covers a second radial quadrant of the lead body corresponding to a radial surface extending from about 45 to 135 degrees around the lead body; a third electrode disposed around the lead body such that it covers a third radial quadrant of the lead body corresponding to a radial surface extending from about 90 to 180 degrees around the lead body; and a fourth electrode disposed around the lead body such that it covers a fourth radial quadrant of the lead body corresponding to a radial surface extending from about 135 to 225 degrees around the lead body.

Example 44 is the implantable lead of any of examples 39-43, wherein the at least one electrode comprising a first and a second electrode extending around the lead body at a radial location corresponding to 0 to 90 degrees and a third and a fourth electrode extending around the lead body at a radial location corresponding to 90 to 180 degrees.

Example 45 is the implantable lead of any of examples 38-44, further comprising an axial locking member configured to secure the sheath in position with respect to the lead body.

Example 46 is the implantable lead of any of examples 39-45, wherein the axial locking member is a nub coupled to the lead body.

Example 47 is the implantable lead of any of examples 39-46, wherein the nub is configured to engage with a recess in the sheath.

Example 48 is the implantable lead of any of examples 39-47 further comprising a radial locking member configured to secure the sheath in position with respect to the lead body at one of a plurality of radial positions around the lead body.

Example 49 is the implantable lead of any of examples 39-48, further comprising at least one stopping member configured to limit axial movement of the sheath over the lead body.

Example 50 is the implantable lead of any of examples 39-49, wherein the at least one stopping member is a ring provided on the lead body.

Example 51 is the implantable lead of any of examples 39-50, wherein the at least one window has a generally helical shape.

Example 52 is the implantable lead of any of examples 39-51, wherein the at least one window has a helical shaped window comprising at least two non-parallel helices.

Example 53 is the implantable lead of any of examples 39-52, wherein the sleeve includes a groove configured to accept a suture for fixing the position of the sheath with respect to the lead body.

Example 54 is the implantable lead of any of examples 39-53, further comprising a second sheath that extends axially over a portion of the first sheath, the second sheath defining a second window.

Example 55 is a method of implanting a medical lead at a tissue site, the method includes providing a lead body including a proximal end portion, a distal end portion and at least one electrode extending circumferentially around at least a portion of the lead body, the lead body including an insulating sheath disposed at the distal end portion, the insulating sheath including at least one exposure window, adjusting at least one of a radial and a longitudinal position of the insulating sheath with respect to the at least one electrode, such that a desired portion of the electrode is exposed, and fixing the position of the insulating sheath with respect to the electrode.

Example 56 is the method of example 55, wherein the at least one window is an electrically permeable window.

Example 57 is an implantable medical lead including a lead body including a proximal end portion and a distal end portion, a first threaded portion between the proximal end portion and the distal end portion and at least one electrode extending substantially around the lead body; and an electrically insulating member that extends axially over a portion of the lead body between the proximal end portion and the distal end portion. The electrically insulating member defines at least one window and is configured to be rotatable around the lead body such that in a first radial position a first portion of the at least one electrode is exposed through the at least one window and a second portion of the at least one electrode is covered by the electrically insulating member. The electrically insulating member further comprising a second threaded portion. The first threaded portion is configured to engage with the second threaded portion to allow both an axial adjustment and a radial adjustment of the electrically insulating member over the lead body.

Example 58 is the implantable lead of example 57, wherein a length of the first threaded portion and a length of the second threaded portion control an amount of linear travel of the electrically insulating member over the lead body and an amount of exposure of the at least one electrode through the at least one window.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as falling within the scope of the claims, together with all equivalents thereof.

We claim:

1. An implantable medical lead for stimulating or sensing a target tissue and minimizing stimulation of a surrounding tissue, the implantable medical lead comprising:
   a lead body including a proximal end portion and a distal end portion, the lead body formed from a flexible and electrically insulative material that defines an outer periphery of the lead body, the lead body further comprising at least one electrode extending circumferentially along the outer periphery of the lead body, the at least one electrode located on the distal end portion of the lead body;
   an insulating sheath disposed over at least a portion of the distal end portion of the lead body and the at least one electrode, the insulating sheath formed from an electrically insulative polymer material and configured to rotate about the lead body and the at least one electrode, the insulating sheath having at least one window adapted to electrically expose at least one portion of the at least one electrode to the target tissue while the electrically insulative polymer material of the sheath simultaneously covers at least one other portion of the at least one electrode to electrically insulate the at least one other portion, wherein the window is formed from a solid, electrically permeable material that allows stimulation energy to pass through the electrically permeable material; and
   at least one protrusion extending radially outward from a portion of the insulating sheath at a location generally opposed to the at least one window the protrusion adapted to urge the electrically exposed at least one portion of the at least one electrode toward the target tissue upon rotation of the insulating sheath with respect to the lead body to shorten a distance between the electrically exposed at least one portion of the at least one electrode and the target tissue;
   wherein the insulating sheath comprises an inner insulating member and an outer insulating member having a compartment, and further wherein the protrusion is disposed on the inner insulating member and is configured to extend at least partially through the compartment.

2. The implantable medical lead of claim 1, wherein rotation of the inner insulating member with respect to the outer insulating member is limited by a contact between the protrusion and an edge of the compartment.

3. An implantable medical lead for stimulating or sensing a target tissue and minimizing stimulation of a surrounding tissue, the implantable medical lead comprising:
   a lead body including a proximal end portion, a distal end portion, and a plurality of spaced-apart electrodes extending circumferentially along an outer periphery of the lead body, the plurality of electrodes located on the distal end portion of the lead body;
   an insulating sheath disposed over at least a portion of the distal end portion of the lead body, the insulating sheath formed from an electrically insulative polymer material and configured to rotate about the lead body and the plurality of electrodes, the insulating sheath having a plurality of windows adapted to electrically expose a portion of each of the plurality of electrodes to the target tissue while the insulative polymer material of the insulating sheath simultaneously covers other portions of the plurality of electrodes to electrically insulate the other portions of the plurality of electrodes, wherein the windows are formed from a solid, electrically permeable material that allows stimulation energy to pass through the electrically permeable material; and
   a plurality of insulating protrusions, each protrusion extending radially outward from a portion of the insulating sheath at a location generally opposed to a corresponding window, each protrusion adapted to urge the electrically exposed portions of the plurality of electrodes towards the target tissue upon rotation of the insulating sheath with respect to the lead body to shorten a distance between the electrically exposed portions of the plurality of electrodes and the target tissue;
   wherein the insulating sheath comprises an inner insulating member and an outer insulating member having a compartment, and further wherein the protrusion is disposed on the inner insulating member and is configured to extend at least partially through the compartment.

* * * * *